United States Patent
Kato et al.

(10) Patent No.: US 6,174,457 B1
(45) Date of Patent: Jan. 16, 2001

(54) COMPOUND HAVING ALKADIENYL GROUP AS SIDE CHAIN, AND LIQUID CRYSTAL COMPOSITION USING SAME

(75) Inventors: Takashi Kato; Kazutoshi Miyazawa; Shuichi Matsui, all of Chiba; Noriyuki Ohnishi, Ibaraki; Takashi Katoh; Yasuyuki Koizumi, both of Kanagawa; Hiroyuki Takeuchi, Chiba; Fusayuki Takeshita, Chiba; Yasusuke Hisatsune, Chiba, all of (JP)

(73) Assignee: Chisso Corporation, Osaka (JP)

( * ) Notice: Under 35 U.S.C. 154(b), the term of this patent shall be extended for 0 days.

(21) Appl. No.: 09/242,333

(22) PCT Filed: Sep. 22, 1997

(86) PCT No.: PCT/JP97/03347

§ 371 Date: Feb. 11, 1999

§ 102(e) Date: Feb. 11, 1999

(87) PCT Pub. No.: WO98/13321

PCT Pub. Date: Apr. 2, 1998

(30) Foreign Application Priority Data

Sep. 27, 1996 (JP) .................................................. 8-277596

(51) Int. Cl.[7] .......................... C09K 19/30; C09K 19/06; C09K 19/12; C07C 13/20; C07C 19/34

(52) U.S. Cl. .................................. 252/299.63; 299/299.6; 299/299.66; 299/299.67; 299/299.61; 585/23; 585/25

(58) Field of Search ..................... 252/299.61, 299.63, 252/299.67, 299.66, 299.6; 585/23, 25

(56) References Cited

U.S. PATENT DOCUMENTS

| | | | |
|---|---|---|---|
| 5,013,477 | * 5/1991 | Buchecker et al. | 252/299.63 |
| 5,449,810 | * 9/1995 | Fujita et al. | 559/425 |
| 5,653,911 | 8/1997 | Kondo et al. | 252/299.01 |
| 5,976,404 | * 11/1999 | Hirschmann et al. | 252/299.01 |
| 5,989,452 | * 11/1999 | Kato et al. | 252/299.63 |
| 5,997,767 | * 12/1999 | Hirschmann et al. | 252/299.63 |
| 6,001,275 | * 12/1999 | Ohnishi et al. | 252/299.01 |

FOREIGN PATENT DOCUMENTS

| | | |
|---|---|---|
| 195 20 246 | 12/1995 | (DE) . |
| 0 501 268 | 2/1992 | (EP) . |
| 0501268 A2 | 9/1992 | (EP) . |
| 0805134 A1 | 5/1997 | (EP) . |
| 0 805 134 | 11/1997 | (EP) . |
| 61-83136 | 4/1986 | (JP) . |
| 4-502627 | 5/1992 | (JP) . |
| 6-500343 | 1/1994 | (JP) . |
| WO 9622261 A1 | 7/1996 | (WO) . |
| 97/13821 | 4/1997 | (WO) . |
| WO 9713821 A1 | 4/1997 | (WO) . |

OTHER PUBLICATIONS

"Polar Alkenyls: Physical Properties and Correlations with Molecular Structure of New Nematic Liquid Crystals", by M. Schadt et al., Mol. Cryst. Liq. Cryst., 1985, vol. 122, pp. 241–260.

* cited by examiner

Primary Examiner—C. H. Kelly
(74) Attorney, Agent, or Firm—McDermott, Will & Emery

(57) ABSTRACT

A compound represented by the general formula (1)

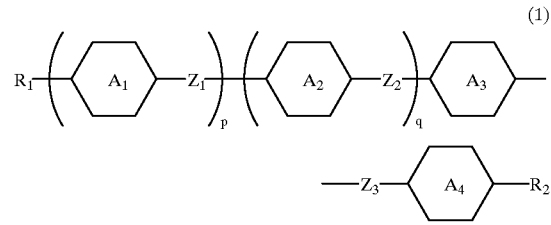

wherein $R_1$ is an alkadienyl group having 4 to 10 carbon atoms in which a hydrogen atom may be substituted by a fluorine atom or the like; $R_2$ is an alkenyl group having 2 to 10 carbon atoms in which a hydrogen atom may be substituted by a fluorine atom or the like; one or more non-adjacent methylene groups (—$CH_2$—) in the alkadienyl group or the alkenyl group may be replaced by —O— or the like; rings $A_1$, $A_2$, $A_3$ and $A_4$ are each 1,4-cyclohexylene, 1,4-phenylene or the like in which a hydrogen atom may be substituted by a halogen atom; $Z_1$, $Z_2$ and $Z_3$ are each a single bond, —$CH_2CH_2$—, —CF═CF— or the like; p and q are each 0 or 1. The above compound has a large elastic constant ratio, steep electro-optic characteristics and a little temperature dependence in a low temperature range, and so it is useful for the manufacture of a liquid crystal display device.

20 Claims, No Drawings

COMPOUND HAVING ALKADIENYL GROUP AS SIDE CHAIN, AND LIQUID CRYSTAL COMPOSITION USING SAME

TECHNICAL FIELD

The present invention relates to a novel liquid crystal compound useful as a liquid crystal material for a display device. More specifically, it relates to a novel liquid crystal compound which has a low viscosity, a mutually good solubility with another liquid crystal compound and a proper optical anisotropy (Δn) and which can obtain sharp electro-optical properties in the case that it is used in a liquid crystal display device, a liquid crystal composition containing this compound, and a liquid crystal display device.

BACKGROUND ART

Heretofore, as liquid crystal compounds which can suitably be used in a super-twisted nematic device (heretofore abbreviated to "the STN device" sometimes), various compounds having an alkenyl group as a side chain have been synthesized, and some of these compounds have practically been used. For example, compounds represented by the following formulae (s-i) to (s-3) are disclosed in Mol. Cryst. Liq. Cryst., Vol. 122, p. 241 (1985) and Japanese Patent Application Laid-open No. 83136/1986, compounds represented by the following formulae (s-4) and (s-5) are disclosed in Japanese Patent Application Laid-open No. 92740/1994, and compounds represented by the following formulae (s-6) and (s-7) are disclosed in DE 19520246A1. Furthermore, compounds represented by the following formulae (s-8) and (s-9) in which a fluorine atom is directly bonded to a double bond are disclosed in Japanese PCT Patent Application Laid-open No. 500343/1994, and a compound represented by the following formula (s-10) is disclosed in Japanese PCT Patent Application Laid-open No. 502627/1992.

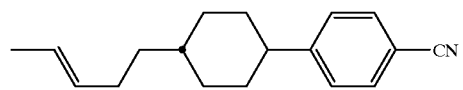
(s-1)

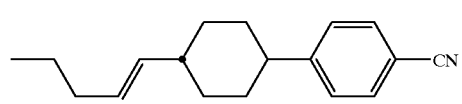
(s-2)

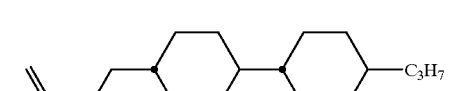
(s-3)

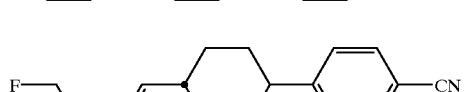
(s-4)

(s-5)

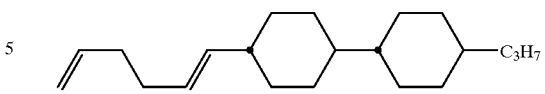
(s-6)

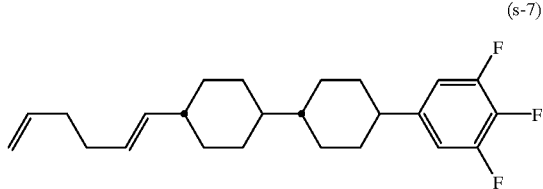
(s-7)

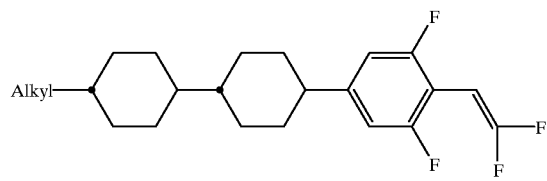
(s-8)

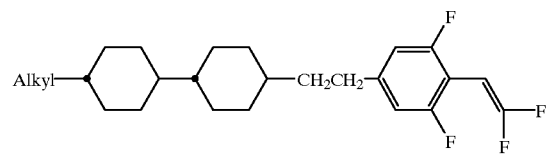
(s-9)

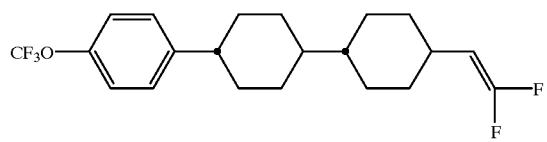
(s-10)

However, the compounds represented by the formulae (s-1) to (s-7) all have strong inclination to show a smectic phase, so that it is difficult on occasion to use a large amount of the compound in a liquid crystal composition. In addition, the compounds represented by the formulae (s-4) to (s-7) have a high viscosity, and the compounds represented by the formulae (s-8) to (s-10) contain some portions which should be improved. For example, they are poor in chemical stability (particularly heat stability) on occasion. In particular, the improvement of a steepness of electro-optic characteristics is still desired.

DISCLOSURE OF THE INVENTION

The present inventors have intensively investigated to solve the above problems, and as a result, it has been found that a compound having an alkadienyl group at one terminal and an alkenyl group at the other terminal of its molecule has an extremely large elastic constant ratio ($K_{33}/K_{11}$), a very low viscosity, a wide nematic phase temperature range, a high chemical stability, a proper optical anisotropy (Δn) and dielectric anisotropy (Δε). Furthermore, it has also been found that when a liquid crystal composition containing this kind of compound is used, there can be manufactured a liquid crystal display device having steep electro-optic characteristics, a short response time, a wide operation temperature range and a low driving voltage, and therefore, the above compound is suitable for a liquid crystal composition for liquid crystal display devices, particularly STN (super-twisted nematic) devices which are now extensively used. In consequence, the present invention has been completed.

Accordingly, an object of the present invention is to provide a liquid crystal compound having a low viscosity, a mutually good solubility with another liquid crystal compound, a proper optical anisotropy (Δn), a proper dielectric anisotropy (Δε) and steep electro-optic characteristics. Another object of the present invention is to provide a liquid crystal composition using this compound. Still another object of the present invention is to provide a liquid crystal display device.

In the present invention, the term "liquid crystal compound" means a compound showing a liquid crystal phase and a compound which does not show the liquid crystal phase by itself but which exhibits suitable characteristics as a liquid crystal when mixed to form a liquid crystal composition.

A compound represented by the following formula (s-11) having an alkadienyl group as a side chain is disclosed in Japanese Patent Application No. 310039/1995, and a compound represented by the following formula (s-12) simultaneously having alkenyl groups at both the terminals thereof is disclosed in DE414647A1. However, there have not been any concrete description of a compound having an alkadienyl group at one terminal and an alkenyl group at the other terminal of its molecule. Furthermore, Japanese PCT Patent Application Laid-open No. 502627/1992 discloses a compound alone in which a terminal group is a polar group such as a halogen atom, and it does not disclose the compound simultaneously having the alkadienyl group and the alkenyl group.

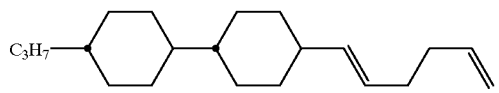
(s-11)

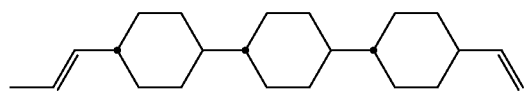
(s-12)

The aspects of the present invention will be described in the following paragraphs [1] to [15].

[1] A compound represented by the general formula (1)

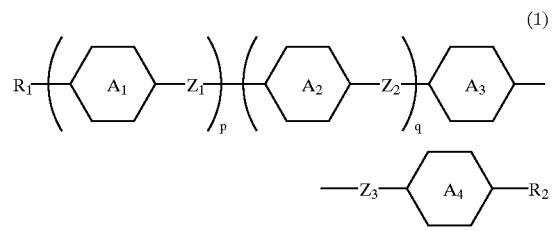
(1)

wherein $R_1$ is an alkadienyl group having 4 to 10 carbon atoms in which at least one hydrogen atom may be substituted by a fluorine atom, a chlorine atom or a cyano group; $R_2$ is an alkenyl group having 2 to 10 carbon atoms in which at least one hydrogen atom may be substituted by a fluorine atom, a chlorine atom or a cyano group; one or more non-adjacent methylene groups (—$CH_2$—) in the alkadienyl group or the alkenyl group may be replaced by —O—, —CH=CH— or —C≡C—; rings $A_1$, $A_2$, $A_3$ and $A_4$ are each independently 1,4-cyclohexylene, 1,4-cyclohexenylene, 1,4-phenylene, 1,3-dioxane-2,5-diyl, pyridine-2,5-diyl or pyrimidine-2,5-diyl in which at least one hydrogen atom may be substituted by a halogen atom; $Z_1$, $Z_2$ and $Z_3$ are each independently a single bond, —$CH_2CH_2$—, —CH=CH—, —C≡C—, —$CH_2O$—, —$OCH_2$—, —$(CH_2)_4$—, —$(CH_2)_3$—O—, —O—$(CH_2)_3$—, —$(CH_2)_2$—CH=CH—, —CH=CH—$(CH_2)_2$—, —$CF_2O$—, —$OCF_2$—, —CR=CH—, —CH=CR— or —CF=CF—, and R is an alkyl group having 1 to 5 carbon atoms; p and q are each independently 0 or 1; and each element in the formula may be substituted by its isotope.

[2] The compound according to the above paragraph [1] wherein $R_1$ is a 1,3-alkadienyl group; and $R_2$ is an alkenyl group.

[3] The compound according to the above paragraph [1] wherein $R_1$ is a 1,4-alkadienyl group; and $R_2$ is an alkenyl group.

[4] The compound according to the above paragraph [1] wherein $R_1$ is a 1,5-alkadienyl group; and $R_2$ is an alkenyl group.

[5] The compound according to the above paragraph [1] wherein $R_1$ is a 1,6-alkadienyl group; and $R_2$ is an alkenyl group.

[6] The compound according to the above paragraph [1] wherein $R_1$ is a 3,7-alkadienyl group; and $R_2$ is an alkenyl group.

[7] The compound according to the above paragraph [1] wherein $R_1$ and $R_2$ are each an alkadienyl group.

[8] A liquid crystal composition comprising two or more components which contains at least one of the compounds described in the above paragraphs [1] to [7].

[9] A liquid crystal composition which comprises, as a first component, at least one of the compounds described in the above paragraphs [1] to [7], and as a second component, at least one compound selected from the group consisting of compounds represented by the general formulae (2), (3) and (4)

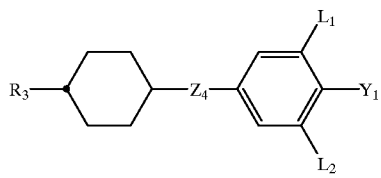

(2)

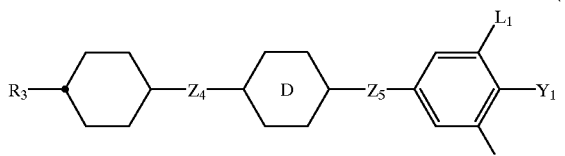

(3)

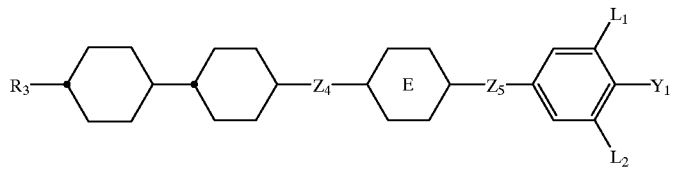

(4)

wherein $R_3$ is an alkyl group having 1 to 10 carbon atoms in which at least one hydrogen, atom may be substituted by a fluorine atom, and one or more non-adjacent methylene groups (—$CH_2$—) in the alkyl group may be replaced by —O— or —CH=CH—; $Y_1$ is a fluorine atom, a chlorine atom, $OCF_3$, $OCF_2H$, $CF_3$, $CF_2H$, $CFH_2$, $OCF_2CF_2H$ or $OCF_2CFHCF_3$; $L_1$ and $L_2$ are each independently a hydrogen atom or a fluorine atom; $Z_4$ and $Z_5$ are each independently a 1,2-ethylene group, a 1,4-butylene group, —COO—, —$CF_2O$—, —$OCF_2$—, —CH=CH— or a single bond; a ring D is trans-1,4-cyclohexylene, 1,3-dioxane-2,5-diyl or 1,4-phenylene in which at least one hydrogen atom may be substituted by a fluorine atom; a ring E is trans-1,4-cyclohexylene or 1,4-phenylene in which at least one hydrogen atom may be substituted by a fluorine atom; and each element in the formulae may be substituted by its isotope.

[10] A liquid crystal composition which comprises, as a first component, at least one of the compounds described in the above paragraphs [1] to [7], and as a second component, at least one compound selected from the group consisting of compounds represented by the general formulae (5) and (6)

(5)

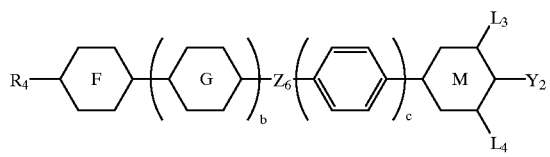

(6)

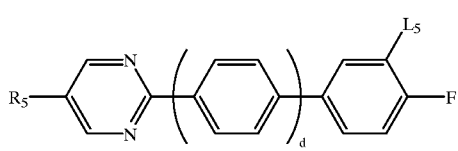

wherein $R_4$ and $R_5$ are each independently an alkyl group having 1 to 10 carbon atoms in which at least one hydrogen atom may be substituted by a fluorine atom, and one or more non-adjacent methylene groups (—$CH_2$—) in the alkyl group may be replaced by —O— or —CH=CH—; $Y_2$ is a —CN group or —C≡—C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene in which at least one hydrogen atom may be substituted by a fluorine atom, or pyrimidine-2,5-diyl; a ring M is trans-1,4-cyclohexylene or 1,4-phenylene; $Z_6$ is a 1,2-ethylene group, —COO— or a single bond; $L_3$, $L_4$ and $L_5$ are each independently a hydrogen atom or a fluorine atom; b, c and d are each independently 0 or 1; and each element in the formulae may be substituted by its isotope.

[11] A liquid crystal composition which comprises, as a first component, at least one of the compounds described in the above paragraphs [1] to [7]; as a second component, at least one compound selected from the group consisting of the compounds represented by the above general formulae (2), (3) and (4); and as a third component, at least one compound selected from the group consisting of compounds represented by the general formulae (7), (8) and (9)

(7)

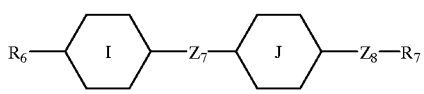

(8)

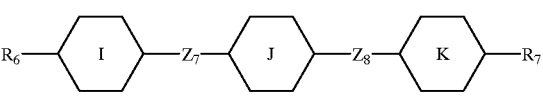

(9)

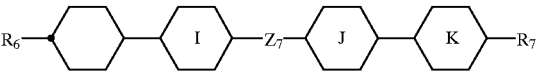

wherein $R_6$ and $R_7$ are each independently an alkyl group having 1 to 10 carbon atoms in which at least one hydrogen atom may be substituted by a fluorine atom, and one or more non-adjacent methylene groups (—$CH_2$—) in the alkyl group may be replaced by —O— or —CH=CH—; I, J and K are each independently trans-1,4-cyclohexylene, pyrimidine-2,5-diyl or 1,4-phenylene in which a hydrogen atom may be substituted by a fluorine atom; $Z_7$ and $Z_8$ are each independently —C≡C—, —COO—, —$CH_2CH_2$—, —CH=CH— or a single bond; and each element in the formulae may be substituted by its isotope.

[12] A liquid crystal composition which comprises, as a first component, at least one of the compounds described in the above paragraphs [1] to [7]; as a second component, at least one compound selected from the group consisting of the compounds represented by the above general formulae (5) and (6); and as a third component, at least one compound selected from the group consisting of the compounds represented by the above general formulae (7), (8) and (9).

[13] A liquid crystal composition which comprises, as a first component, at least one of the compounds described in the above paragraphs [1] to [7]; as a second component, at least one compound selected from the group consisting of the compounds represented by the above general formulae (2), (3) and (4); as a third component, at least one compound selected from the group consisting of the compounds represented by the above general formulae (5) and (6); and as a fourth component, at least one compound selected from the group consisting of the compounds represented by the above general formulae (7), (8) and (9).

[14] A liquid crystal composition which comprises the liquid crystal composition described in any of the above paragraphs [8] to [13], and at least one optically active compound.

[15] A liquid crystal display device which is constituted by the use of the liquid crystal composition described in any of the above paragraphs [8] to [14].

A compound represented by the general formula (1) regarding the present invention has an alkadienyl group at one terminal and an alkenyl group at the other terminal of its molecule, and therefore it can show excellent liquid crystal properties. When this compound is used in a liquid crystal display device, the following advantages can be obtained.

(1) The compound of the present invention has a mutually good solubility with another liquid crystal compound or another liquid crystal composition, and for example, even at a temperature of −20° C. which is practically required, a nematic phase is not impaired.

(2) The compound of the present invention shows a low viscosity, and hence, in preparing a liquid crystal composition, the viscosity of the whole composition does not increase, even when a large amount of the compound is used. In addition, the dependence of the viscosity on a temperature, particularly in a low temperature range, is extremely small as compared with a liquid crystal composition using conventional liquid crystal compounds. By the use of the liquid crystal compound of the present invention, the liquid crystal composition having a high-speed response performance can be prepared.

(3) The compound of the present invention is very chemically stable, and the liquid crystal composition in which this compound is used has a very high specific resistance value and voltage holding ratio. This compound is also remarkably stable to external factors such as ultraviolet light and heat, and hence it shows a chemical stability which is satisfactory as a constitutional element of the practical liquid crystal composition.

(4) As compared with a liquid crystal composition using a conventional liquid crystal compound, the liquid crystal composition using the compound of the present invention has a much higher elastic constant ratio ($K_{33}/Kll$), steeper electro-optic characteristics and an extremely smaller dependence of the above constant ratio on a temperature particularly in a low temperature range.

BEST MODE FOR CARRYING OUT THE INVENTION

A compound represented by the general formula (1) of the present invention is useful as a component of a liquid crystal composition which can be utilized to manufacture liquid crystal display devices.

The definition of the compound represented by the general formula (1) is as given hereinbefore. $R_1$, $R_2$ and the like of this compound represented by the general formula (1) can suitably be selected, whereby the liquid crystal compound or the liquid crystal composition having desired physical properties can be obtained.

In order to obtain the liquid crystal composition having the particularly high elastic constant ratio ($K_{33}/K_{11}$), $R_1$ in the general formula (1) is preferably a 1,3-alkadienyl group, a 1,4-alkadienyl group, a 1,5-alkadienyl group, a 1,6-alkadienyl group or a 3,7-alkadienyl group, and $R_2$ is preferably a 1-alkenyl group, a 2-alkenyl group or a 3-alkenyl group. Furthermore, $R_2$ may be the alkadienyl group, but in this case, the preferable alkadienyl group is a 1,3-alkadienyl group, a 1,4-alkadienyl group, a 1,5-alkadienyl group, a 1,6-alkadienyl group or a 3,7-alkadienyl group.

In order to obtain the liquid crystal composition having a low viscosity, rings $A_1$, $A_2$, $A_3$ and $A_4$ are each 1,4-cyclohexylene, 1,3-dioxane-2,5-diyl or 1,4-phenylene which may be substituted by a halogen atom.

In the case that $R_1$ or $R_2$ is a 1-alkadienyl group or a 1-alkenyl group, the compound of the general formula (1) in which the rings $A_1$, $A_2$, $A_3$ and $A_4$ are each 1,4-cyclohexylene, 1,4-cyclohexenylene or 1,3-dioxane-2,5-diyl has a good chemical stability.

In order to obtain the liquid crystal composition having the low viscosity, $Z_1$, $Z_2$ and $Z_3$ are each preferably a single bond, —$CH_2CH_2$—, —CH=CH—, —$(CH_2)_2$—CH=CH—, —CH=CH—$(CH_2)_2$—, —$CF_2O$—, —$OCF_2$— or —CF=CF—, and more preferably a single bond, —CH=CH—, —$CF_2O$—, —$OCF_2$— or —CF=CF—.

Additionally, in order to obtain the liquid crystal composition having an optical anisotropy (Δn), $Z_1$, $Z_2$ and $Z_3$ each preferably —CH=CH—, —C≡C—, —$(CH_2)_2$—CH=CH—, —CH=CH—$(CH_2)_2$—, —CR=CH—, —CH=CR— or —CF=CF—.

The compound of the present invention can be particularly suitably used in a liquid crystal composition for an STN, but it can also be suitably utilized in other applications. For example, the compound can be suitably used as a liquid crystal compound for twisted nematic (TN) type, guest-host mode (GH) type and polymer dispersion type liquid crystal display devices. In addition, the compound can also be suitably used as a liquid crystal compound for dynamic scattering mode type, active matrix (Δε) type, ferroelectric type and anti-ferroelectric type liquid crystal display devices.

In the case that the compound represented by the general formula (1) is used to prepare the liquid crystal composition, the amount of the compound which is to be contained in the composition is in the range of 0.1 to 99.9% by weight, preferably 1 to 50% by weight, more preferably 3 to 20% by weight. The thus prepared liquid composition has various excellent characteristics.

The liquid crystal composition can be obtained by mixing a first component containing at least one of the compounds represented by the general formula (1) with at least one compound optionally selected from the group consisting of the compounds represented by the general formulae (2) to (9) in compliance with a purpose of the liquid crystal composition.

In the liquid crystal composition for use in the manufacture of an active matrix (Δε) type display device using a thin film transistor (TFT), a high reliability is required, and for example, a positive dielectric anisotropy (Δε), an excellent heat stability and chemical stability, and a high voltage holding ratio (or a large specific resistance value) are required. In preparing the liquid crystal composition which can meet the above requirements, the compounds represented by the general formulae (2) to (4) are very suitable.

Among the compounds represented by the general formulae (2) to (4), examples of the preferable compounds include compounds (2-1) to (2-9), (3-1) to (3-69) and (4-1) to (4-24).
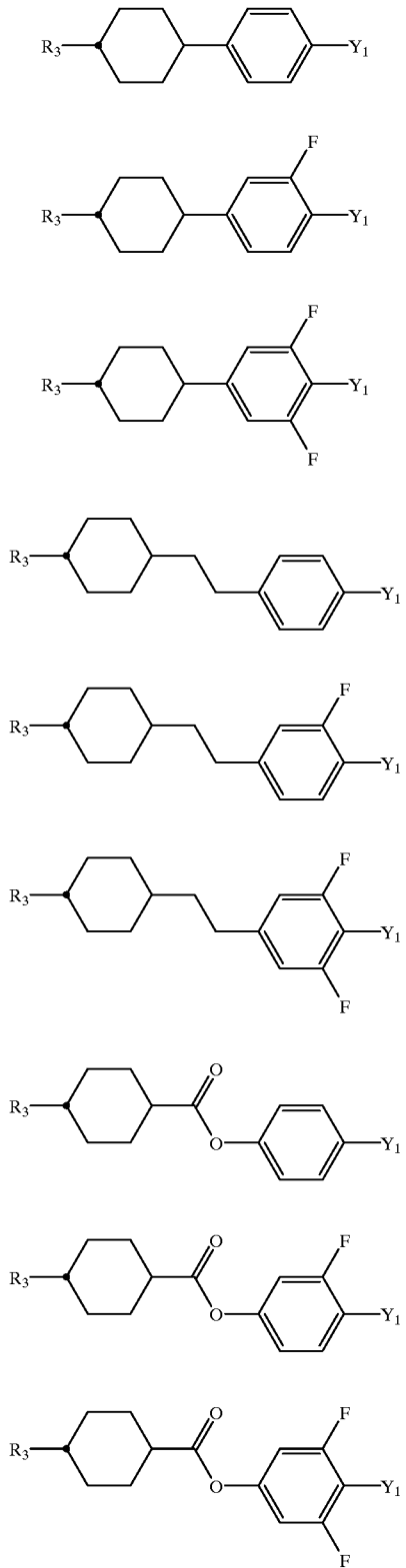
(2-1), (2-2), (2-3), (2-4), (2-5), (2-6), (2-7), (2-8), (2-9)
-continued
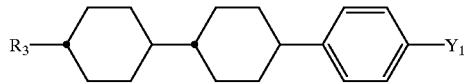
(3-1)
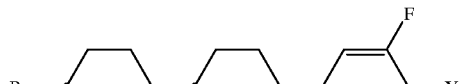
(3-2)
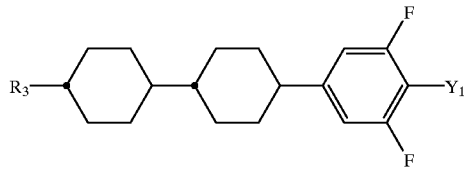
(3-3)
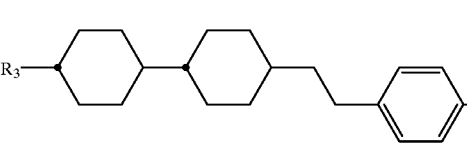
(3-4)
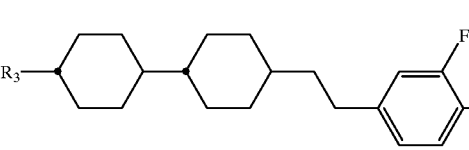
(3-5)
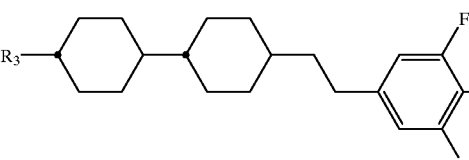
(3-6)
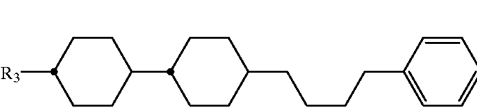
(3-7)
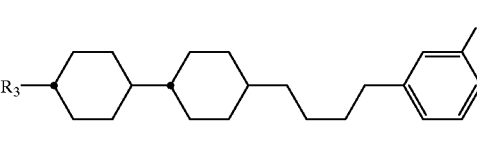
(3-8)
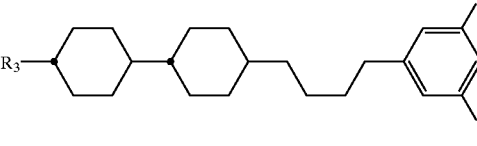
(3-9)

(3-10) 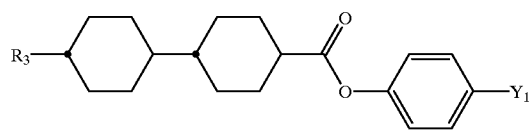
(3-11) 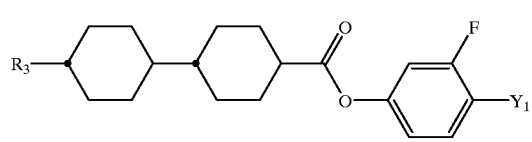
(3-12) 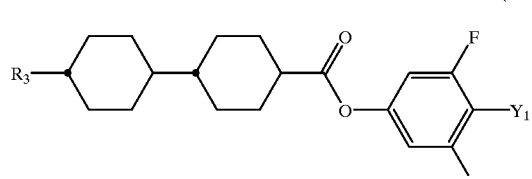
(3-13) 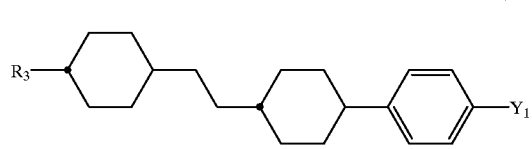
(3-14) 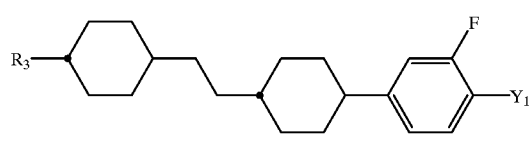
(3-15) 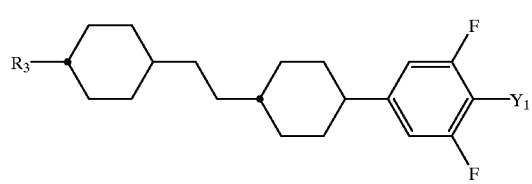
(3-16) 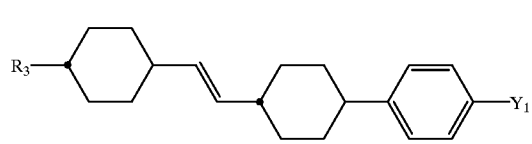
(3-17) 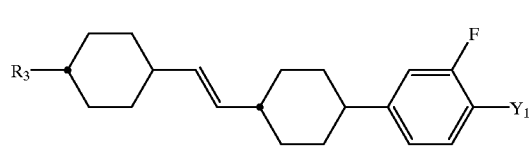
(3-18) 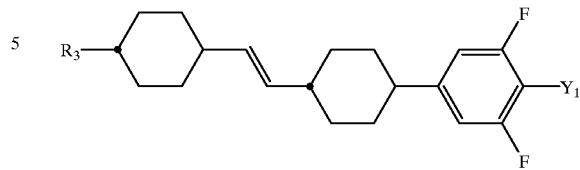
(3-19) 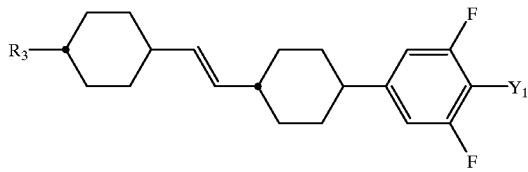
(3-20)
(3-21)
(3-22)
(3-23)
(3-24)
(3-25)
(3-26) 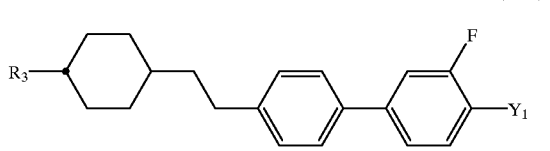

(3-27)
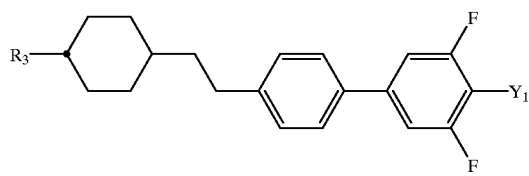
(3-28)
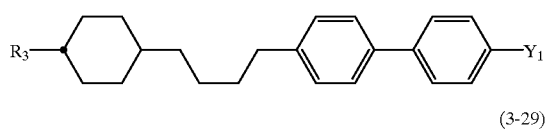
(3-29)
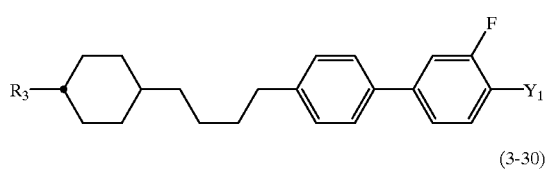
(3-30)
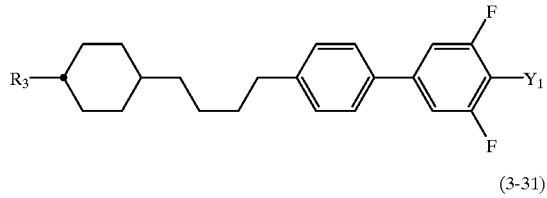
(3-31)
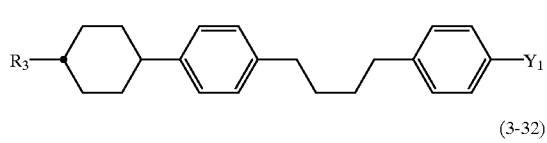
(3-32)
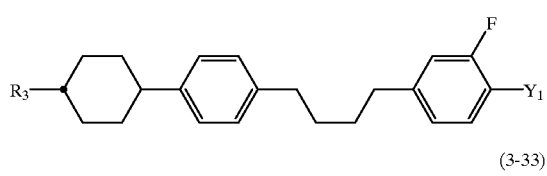
(3-33)
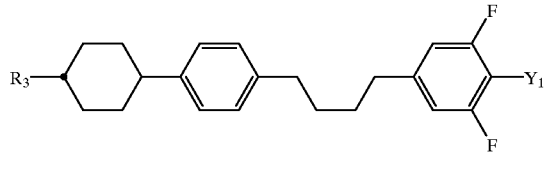
(3-34)
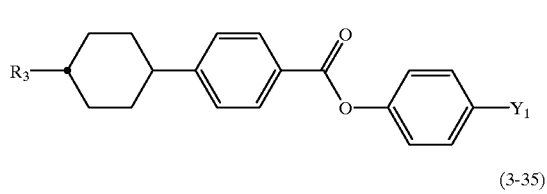
(3-35)
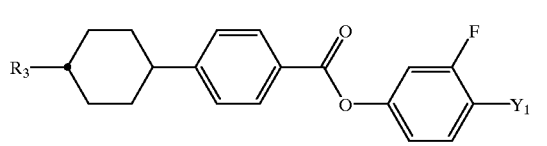
(3-36)
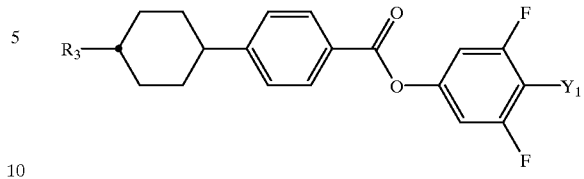
(3-37)
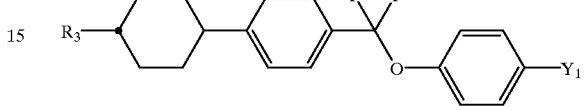
(3-38)
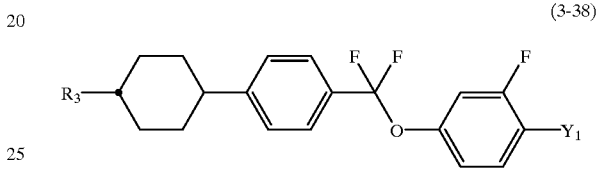
(3-39)
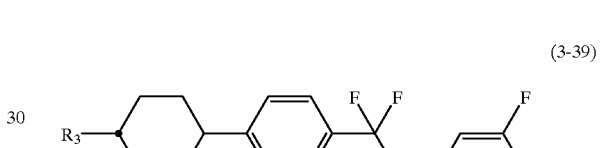
(3-40)
(3-41)
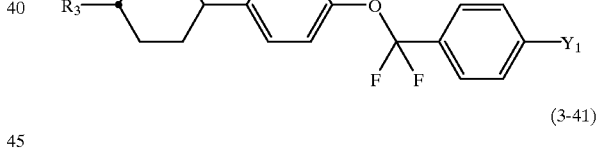
(3-42)
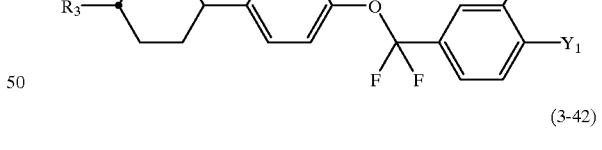
(3-43)
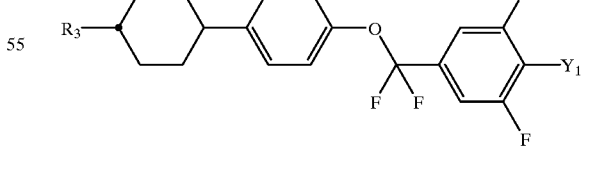

(3-44)
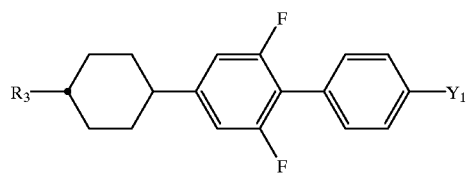
(3-45)
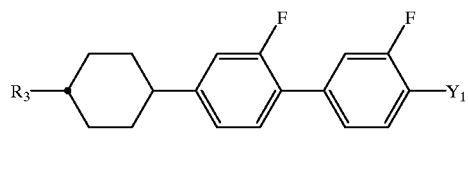
(3-46)
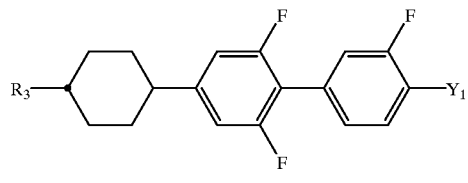
(3-47)
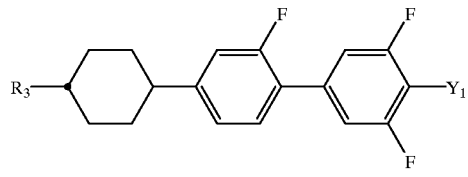
(3-48)
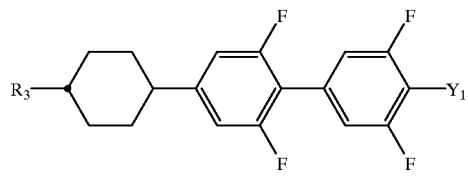
(3-49)
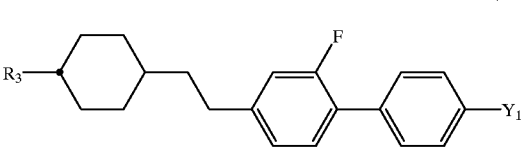
(3-50)
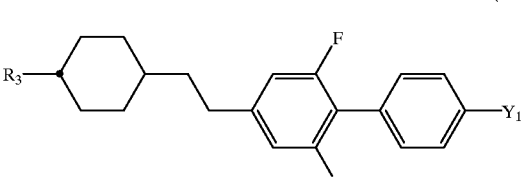
(3-51)
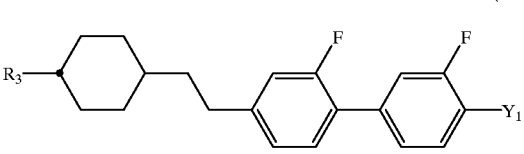
(3-52)
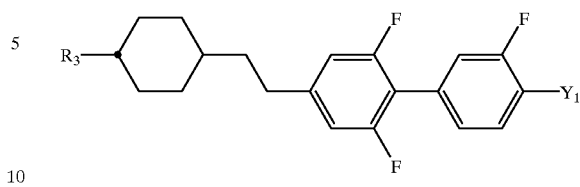
(3-53)
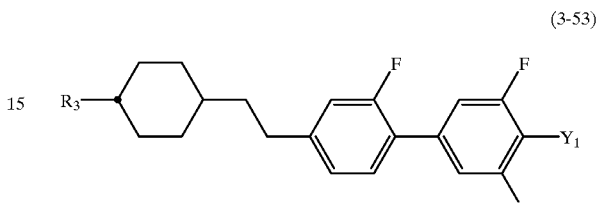
(3-54)
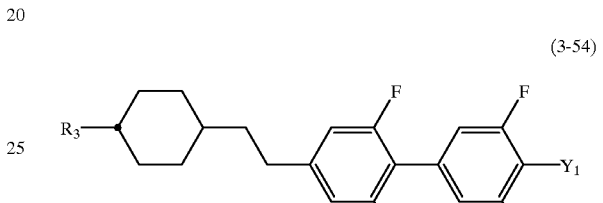
(3-55)
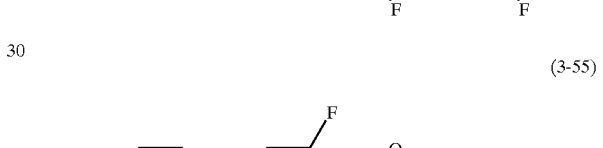
(3-56)
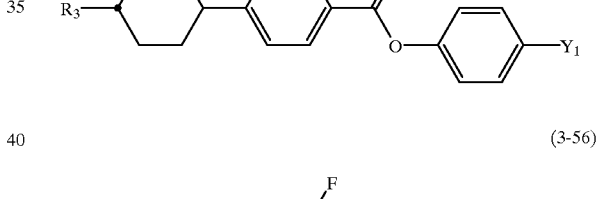
(3-57)
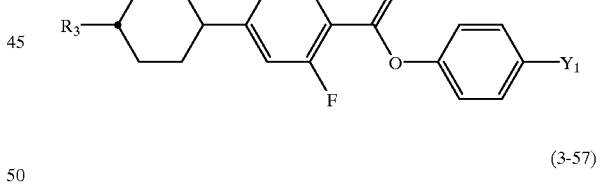
(3-58)
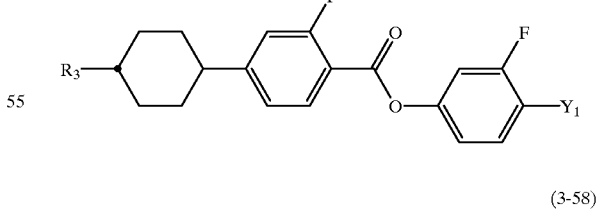

(3-59)
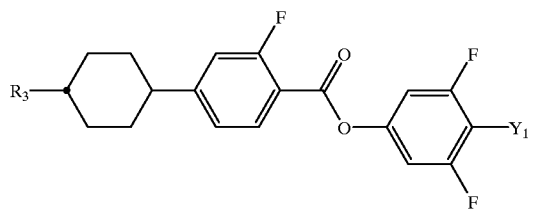
(3-60)
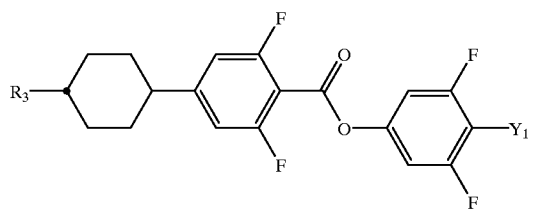
(3-61)
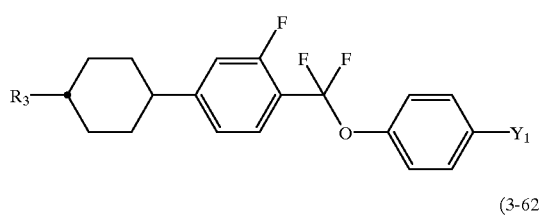
(3-62)
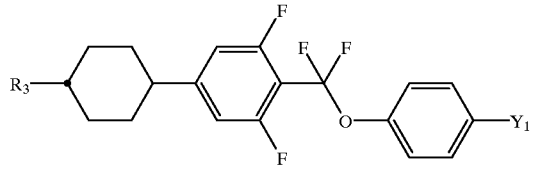
(3-63)
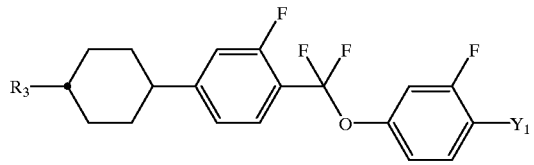
(3-64)
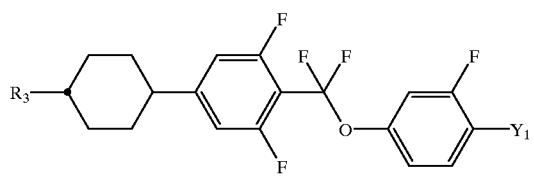
(3-65)
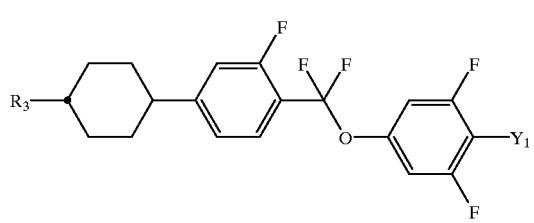
(3-66)
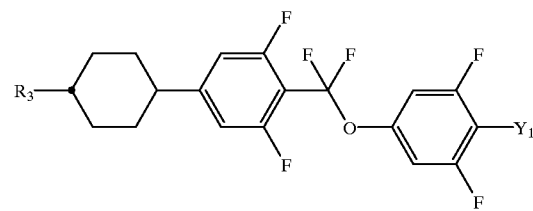
(3-67)
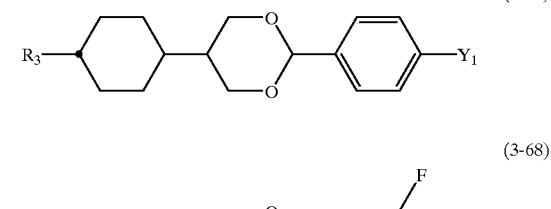
(3-68)
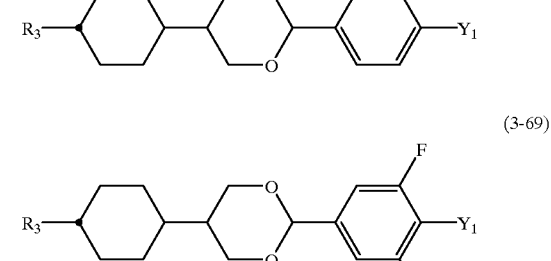
(3-69)
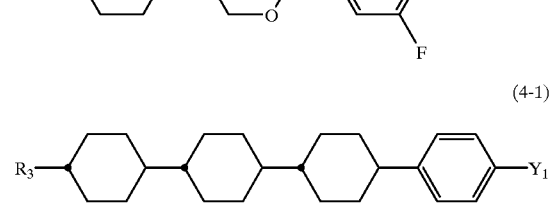
(4-1)
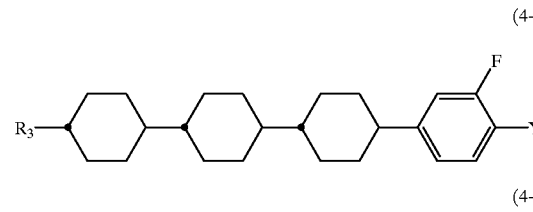
(4-2)
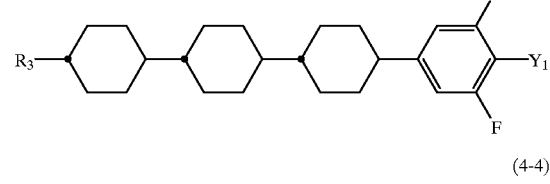
(4-3)
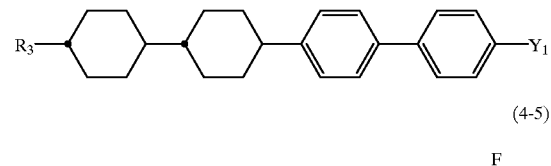
(4-4)
(4-5)
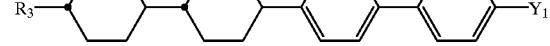

-continued

-continued (4-24)

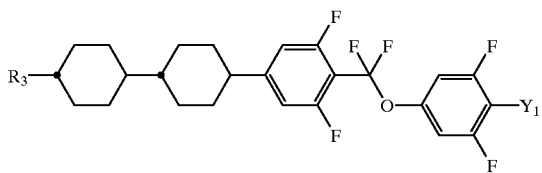

(R₃ and Y₁ are as defined above.)

The compounds represented by the general formulae (2) to (4) can each be used in the range of 1 to 99% by weight, preferably 10 to 97% by weight, more preferably 40 to 95% by weight, based on the total weight of the liquid crystal composition, in the case that the liquid crystal composition for the TFT is prepared.

Furthermore, the compound represented by any of the general formulae (7) to (9) may be contained in the composition in compliance with a purpose.

The compounds represented by the general formulae (2) to (4) are poorer in a function of decreasing a threshold voltage of the liquid crystal composition, as compared with the compounds represented by the general formulae (5) and (6). Therefore, in the case that the liquid crystal composition for an STN display system or a TN display system is prepared, the threshold voltage of the liquid crystal composition inconveniently increases on occasion, if the compound of any of the general formulae (2) to (4) is contained in an amount of 50% by weight or more.

The compounds represented by the general formulae (5) and (6) have a positive and large dielectric anisotropy ($\Delta\epsilon$), and so they can be used particularly for the purpose of decreasing the threshold voltage of the liquid crystal composition. Furthermore, these compounds can also be used for the purpose of expanding a nematic range such as the regulation of the optical anisotropy ($\Delta n$) or the enhancement of a clearing point. When the compound represented by any of the general formulae (5) and (6) is used in the liquid crystal composition for the STN display system or the TN display system, the steepness of its electro-optic characteristics can be improved.

Examples of the compounds which can be preferably used in the manufacture of the liquid crystal composition for the STN display system and the TN display system include compounds represented by the formulae (5-1) to (5-40) and (6-1) to (6-3).

(5-1)
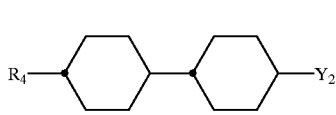

(5-2)
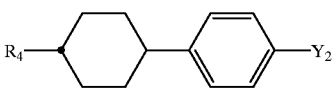

(5-3)
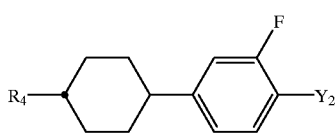

(5-4)
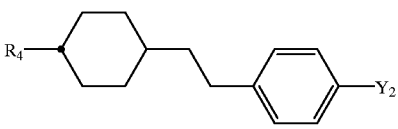

(5-5)
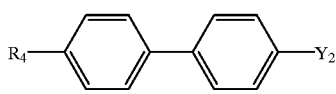

(5-6)
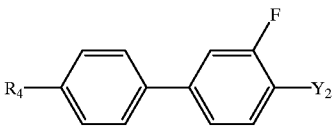

(5-7)
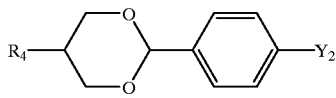

(5-8)
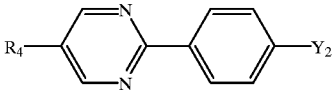

(5-9)
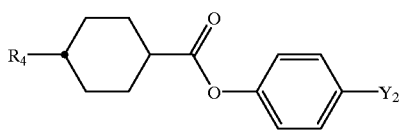

(5-10)
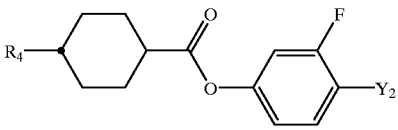

(5-11)
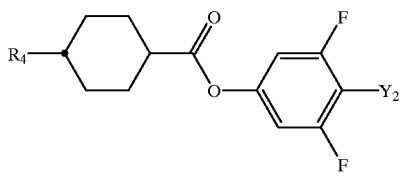

(5-12)
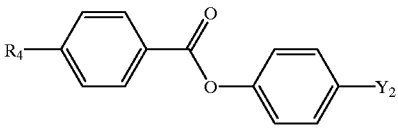

-continued
(5-13)
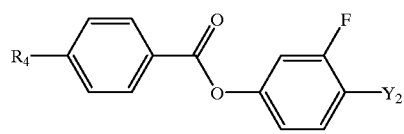
(5-14)
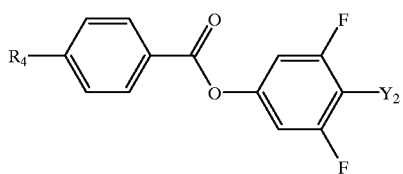
(5-15)
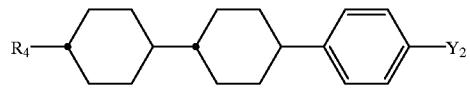
(5-16)
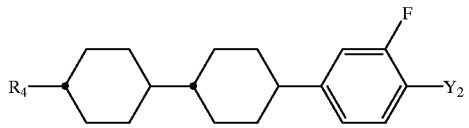
(5-17)
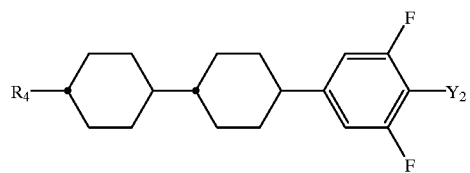
(5-18)
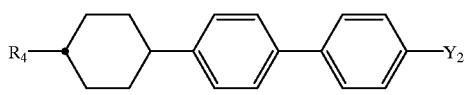
(5-19)
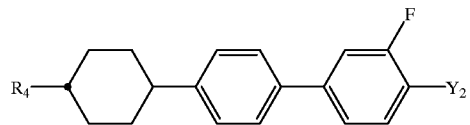
(5-20)
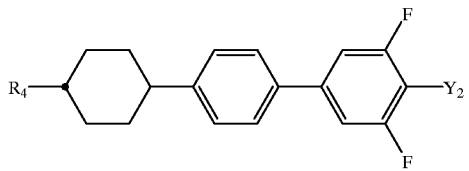
(5-21)
(5-22)
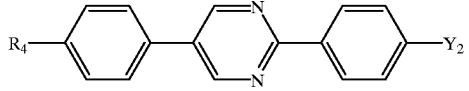
(5-23)
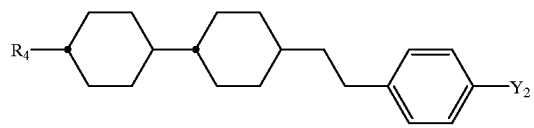
(5-24)
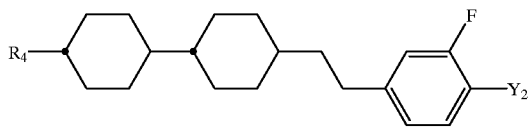
(5-25)
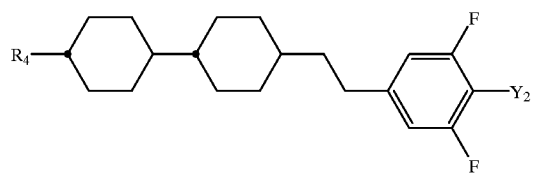
(5-26)
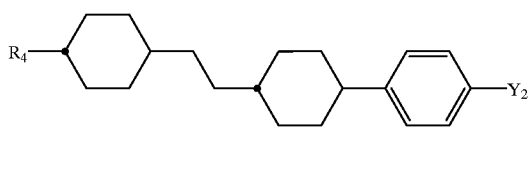
(5-27)
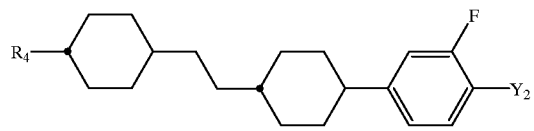
(5-28)
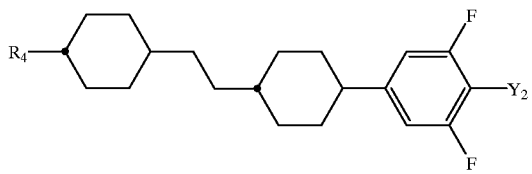
(5-29)
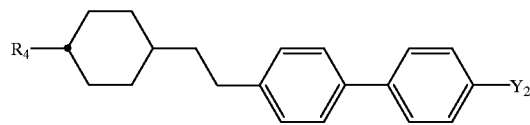
(5-30)
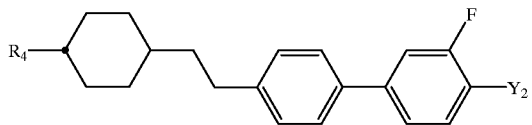

-continued (5-31)
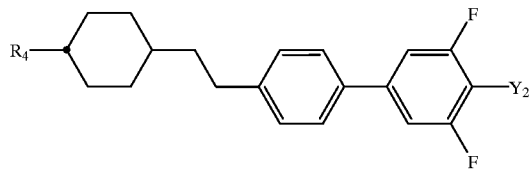

(5-32)
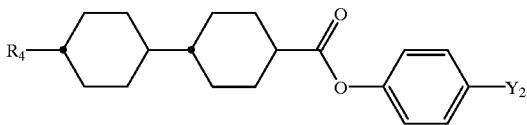

(5-33)
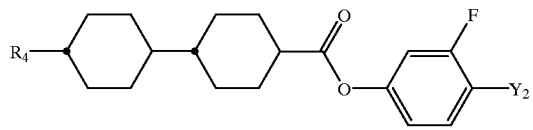

(5-34)
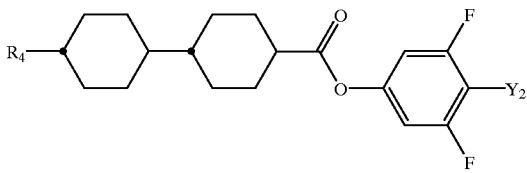

(5-35)
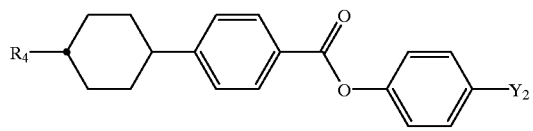

(5-36)
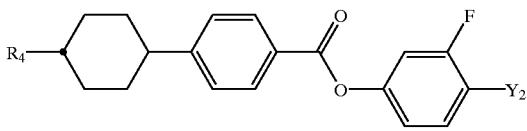

(5-37)
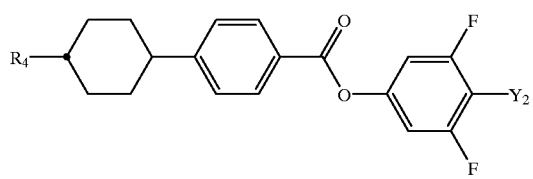

(5-38)
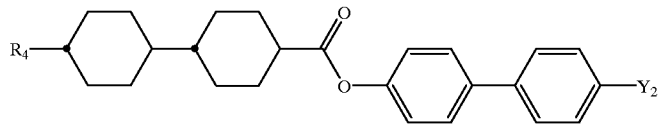

(5-39)
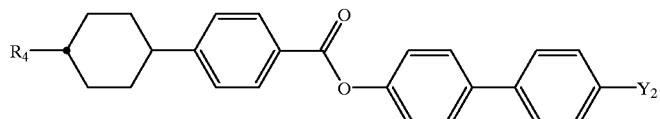

(5-40)
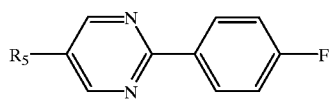

(6-1)
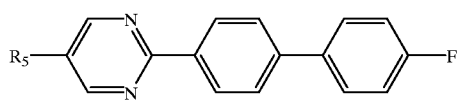

(6-2)

(6-3)

($R_4$, $R_5$ and $Y_2$ are as defined above.)

If the content of the compound represented by any of the general formulae (5) and (6) in the liquid crystal composition increases, the threshold voltage of the liquid crystal composition decreases, and the viscosity increases. Therefore, the liquid crystal compound can be used in large quantities within the required viscosity range, whereby the threshold voltage can be lowered. In the case that the compound is used in the liquid crystal composition for the STN display system and the TN display system, the amount of the compound to be used is in the range of 0.1 to 99.9% by weight, preferably 10 to 97% by weight, more preferably 40 to 95% by weight.

The compounds represented by the general formulae (7) to (9) have small absolute values of the dielectric anisotropy ($\Delta\epsilon$), and so they are substantially neutral compounds. The compounds represented by the general formula (7) can be mainly blended with the liquid crystal composition for the purpose of regulating the viscosity or the optical anisotropy (Δn). Furthermore, the compounds represented by the general formulae (8) and (9) can be blended with the liquid crystal composition for the purpose of expanding the nematic range such as the enhancement of the clearing point or for the purpose of regulating the optical anisotropy (Δn). Preferable examples of the compounds represented by the general formulae (7) to (9) include the compounds represented by the formulae (7-1) to (7-11), (8-1) to (8-18) and (9-1) to (9-6).

(7-1)
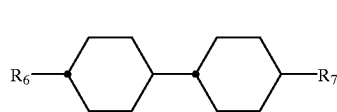

(7-2)
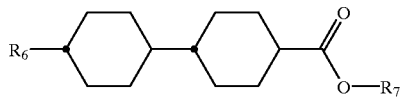

(7-3)
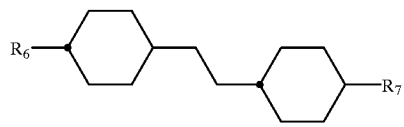

(7-4)
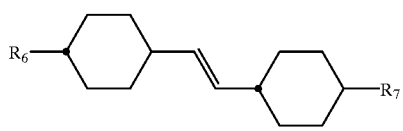

(7-5)
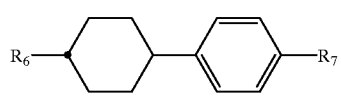

(7-6)
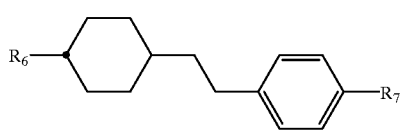

(7-7)
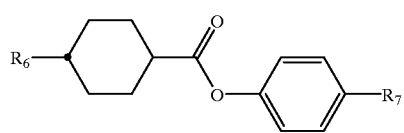

(7-8)
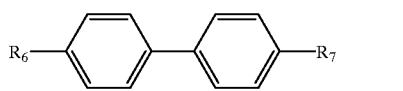

(7-9)
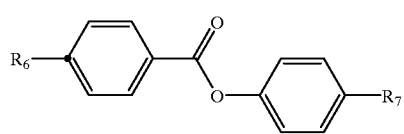

(7-10)
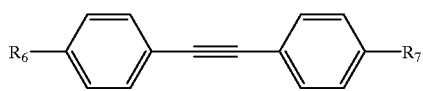

(7-11)
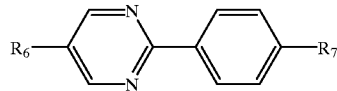

(8-1)
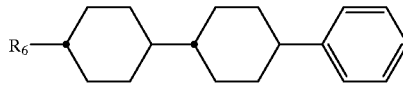

(8-2)
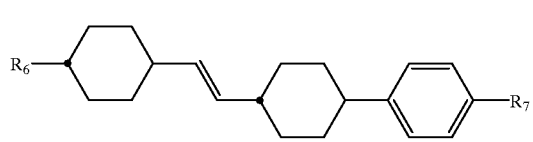

(8-3)
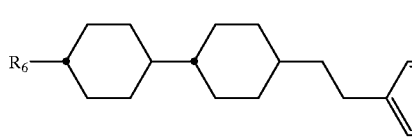

(8-4)
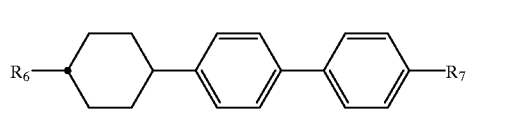

(8-5)
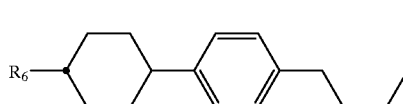

(8-6)
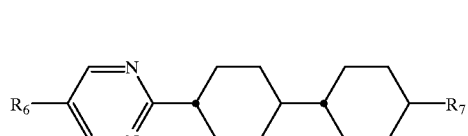

(8-7)
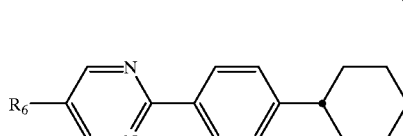

(8-8)
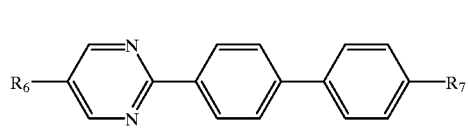

(8-9)
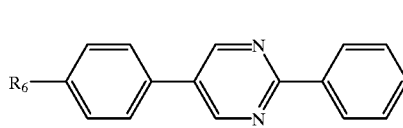

-continued

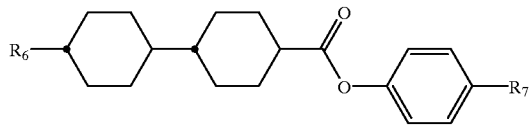
(8-10)

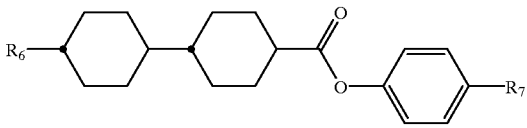
(8-11)

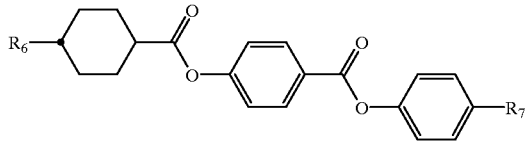
(8-12)

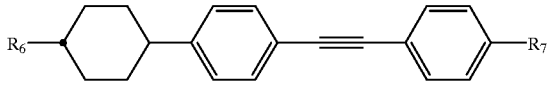
(8-13)

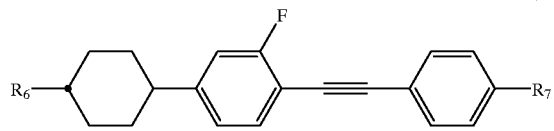
(8-14)

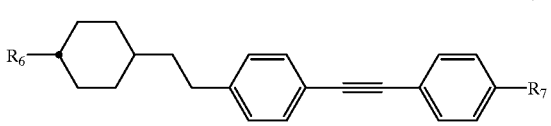
(8-15)

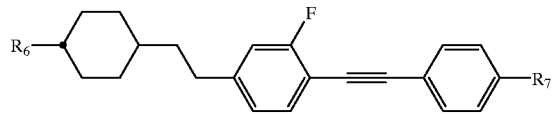
(8-16)

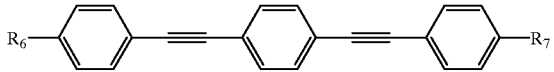
(8-17)

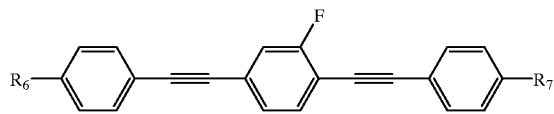
(8-18)

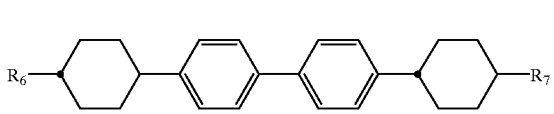
(9-1)

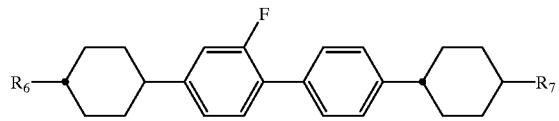
(9-2)

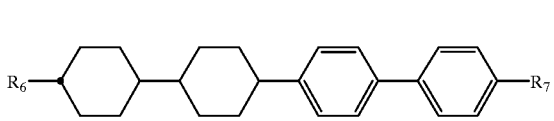
(9-3)

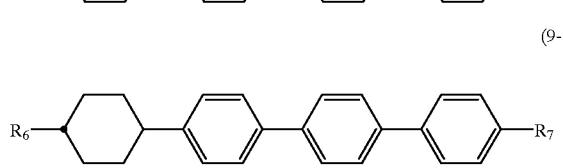
(9-4)

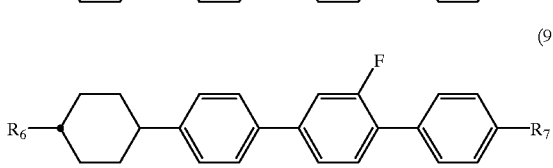
(9-5)

(9-6)

($R_6$ and $R_7$ are as defined above.)

If the amount of the compound represented by any of the general formulae (7) to (9) increases, the threshold voltage of the liquid crystal composition increases, and the viscosity decreases. Therefore, so long as the required value of the threshold voltage of the liquid crystal composition is satisfied, a large amount of the compound can be contained in the liquid crystal composition. In the case that the liquid composition for the TFT is prepared, the amount of the compound to be used is preferably 40% by weight or less, more preferably 35% by weight or less. Furthermore, in the case that the liquid crystal composition for the STN display system or the TN display system is prepared, the amount of the compound to be used is preferably 70% by weight or less, more preferably 60% by weight or less.

Except for a particular case of the liquid crystal composition for an OCB (optically compensated birefringence) mode or the like, an optically active compound can usually be added to the liquid crystal composition in order for the liquid crystal composition to have a helical structure, in order to obtain a necessary twist angle, or in order to prevent a reverse twist. For such a purpose, the conventional known optically active compound can be used. Preferable examples thereof include the optically active compounds represented by the formulae (Op-1) to (Op-8).

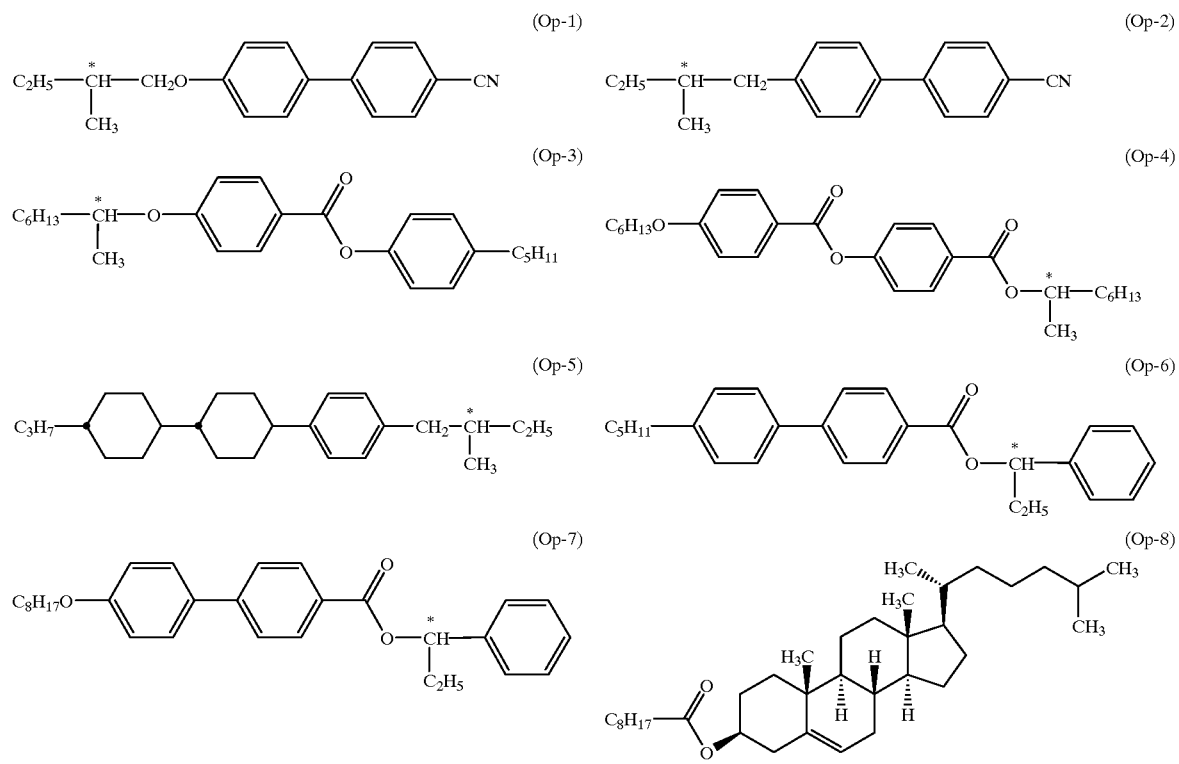

In the present invention, the optically active compound is usually added to the liquid crystal composition to regulate a pitch of the twist. The pitch of the twist is preferably in the range of 40 to 200 μm in the case of the liquid crystal compositions for the TFT and the TN, and preferably in the range of 6 to 20 μm in the case of the liquid crystal composition for the STN. Moreover, in the case of the liquid crystal composition for a bistable TN mode, it is preferable in the range of 1.5 to 4 μm. In addition, for the purpose of improving the dependence of the pitch on a temperature or for another purpose, two or more kinds of optically active compounds may be added.

The liquid crystal composition of the present invention can be prepared by a conventional method. In general, there can be employed a method which comprises mutually dissolving the above various components at a high temperature.

Furthermore, the liquid crystal composition of the present invention can be used as the liquid crystal composition for a guest-host (GH) mode by adding a dichromatic dye thereto. Examples of the dichromatic dye include merocyanine dyes, styryl dyes, azo dyes, azomethine dyes, azoxy dyes, quinophthalone dyes, anthraquinone dyes and tetrazine dyes. Alternatively, there can also be used the liquid crystal composition for NCAP in which micro-capsules of a nematic liquid crystal are used.

In addition, there can also be used the liquid crystal composition for a polymer dispersion type liquid crystal display (PDLCD) typified by a polymer network liquid crystal display (PNLCD) in which a three-dimensional network polymer is formed in the liquid crystal. Moreover, the liquid crystal compositions for an electrically controlled birefringence (ECB) mode and a dynamic scattering (DS) mode can also be used.

The compound of the present invention represented by the general formula (1) can be synthesized by a usual chemical procedure for organic synthesis, for example, by suitably combining procedures described in magazines such as Organic Synthesis, Organic Reactions and Zikken Kagaku Koza.

The introduction of an alkadienyl group moiety can suitably be accomplished by the use of any of methods disclosed in Japanese Patent Application Laid-open No. 286873/1993 and Japanese Patent Application No. 310039/1995.

More concretely, the compound having the alkadienyl group can be synthesized by the following reaction route.

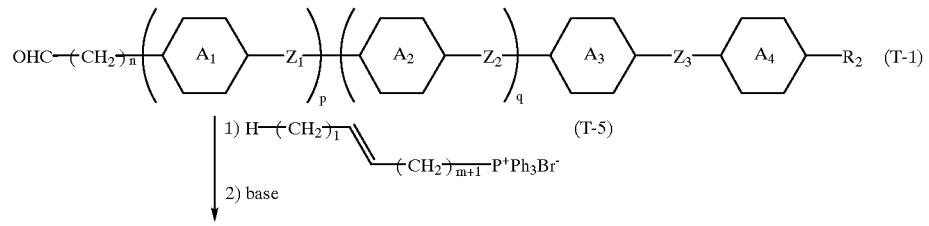

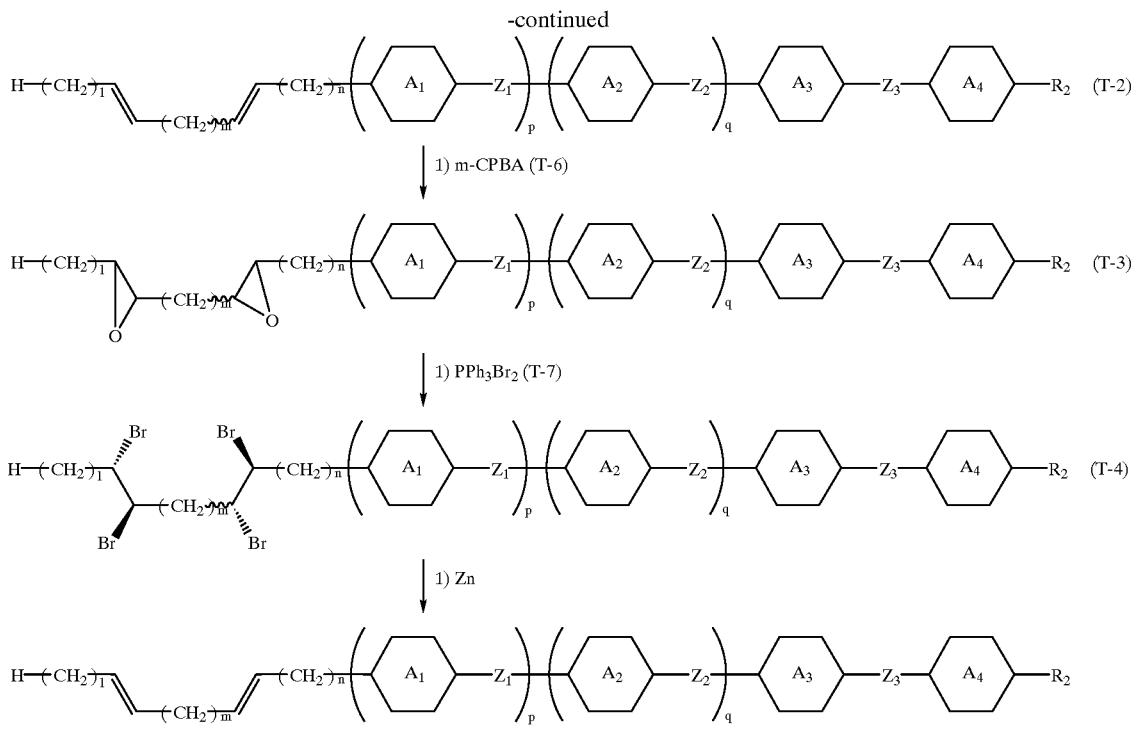

wherein $A_1, A_2, A_3, A_4, p, q, Z_1, Z_2, Z_3$ and $R_2$ are as defined above, and l, m and n are each an integer.

An aldehyde (T-1) is prepared in accordance with any of methods described in Japanese Patent Publication Nos. 2653/1995 and 2654/1995, Japanese Patent Application Laid-open No. 286873/1993 and Japanese Patent Application No. 310039/1995. Next, the thus prepared aldehyde (T-1) is reacted with a ylide obtained from a phosphonium salt (T-5) of an alkenyl halide and a base (e.g., t-BuOK, NaH or the like) to form a cis-olefin (T-2).

Afterward, the cis-olefin (T-2) is reacted with a peroxide (e.g., metachloroperbenzoic acid (T-6), BuOOH, aqueous hydrogen peroxide, performic acid or the like) to convert it into an epoxide (T-3), and this epoxide (T-3) is then reacted with a brominating agent [e.g., dibromotriphenylphospholane (t-7)] to obtain an anti/anti-tetrabromide (T-4). Next, a bromine removal reaction is reducibly carried out, whereby the compound (1) of the present invention can be prepared.

The alkenyl group can be suitably introduced by any of the procedures described in Japanese Patent Publication Nos. 2653/1995 and 2654/1995, Japanese Patent Application Laid-open No. 286873/1993 and Japanese Patent Application No. 310039/1995.

The synthesis can also be accomplished by the following reaction route.

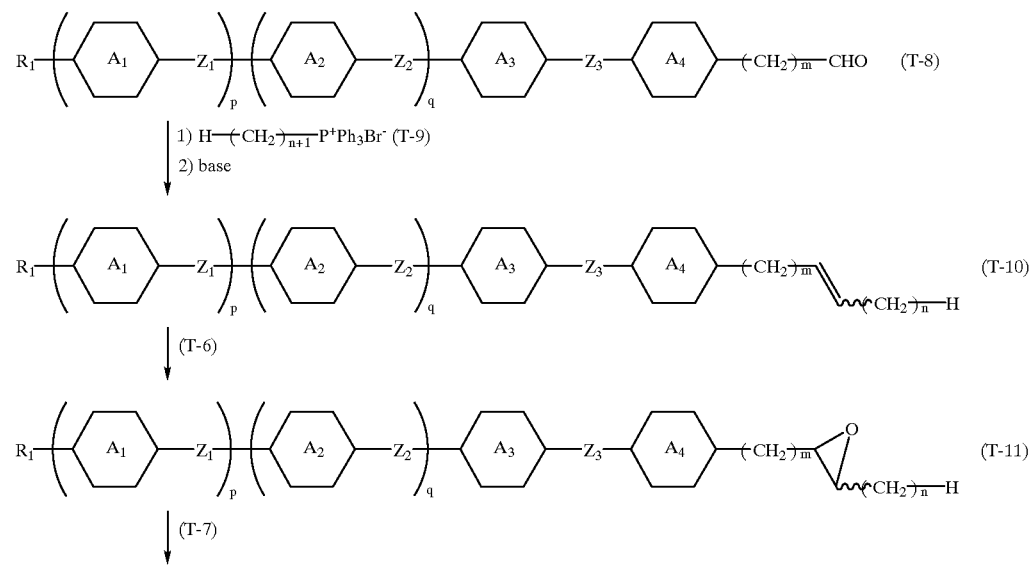

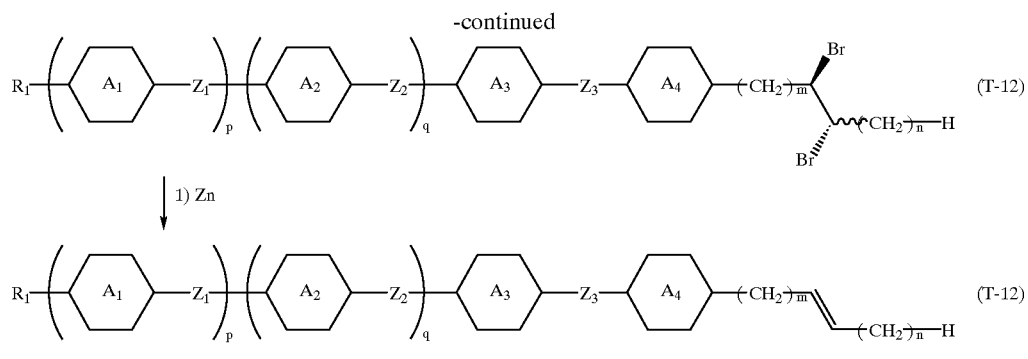

wherein $A_1$, $A_2$, $A_3$, $A_4$, p, q, $Z_1$, $Z_2$, $Z_3$ and $R_1$ are as defined above, and l, m and n are each an integer.

An aldehyde (T-8) is prepared in accordance with any of the methods described in Japanese Patent Publication Nos. 2653/1995 and 2654/1995, Japanese Patent Application Laid-open No. 286873/1993 and Japanese Patent Application No. 310039/1995. Next, the thus prepared aldehyde (T-8) is reacted with a ylide obtained from a phosphonium salt (T-9) of an alkenyl halide and a base (e.g., t-BuOK, NaH or the like) to form a cis-olefin (T-10). Afterward, the cis-olefin (T-10) is reacted with a peroxide (e.g., metachloroperbenzoic acid (T-6), BuOOH, aqueous hydrogen peroxide, performic acid or the like) to convert it into an epoxide (T-11), and this epoxide (T-11) is then reacted with a brominating agent (e.g., dibromotriphenylphospholane) to obtain an anti-dibromide (T-12). Next, a bromine removal reaction is reducibly carried out, whereby the compound (1) of the present invention can be synthesized.

Next, the present invention will be described in more detail with reference to examples.

EXAMPLE 1

4'-(1,5-hexadienyl)-4-(3-butenyl)bicyclohexane [a compound having the general formula (1) in which $R_1$ is 1,5-hexadienyl, $R_2$ is 3-butenyl, p=q=0, ring $A_3$=ring $A_4$ is 1,4-cyclohexylene, and $Z_3$ is a single bond] was prepared in accordance with the following synthetic scheme.

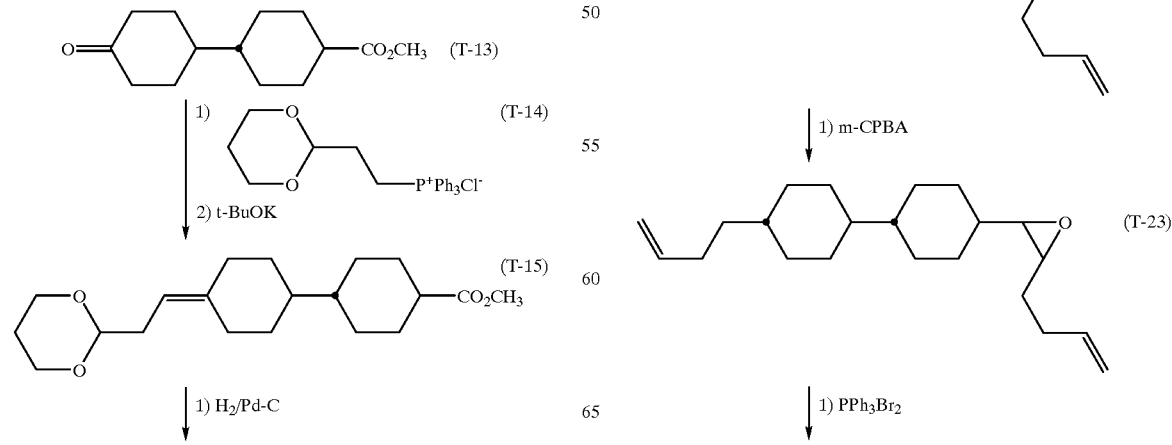

37

-continued

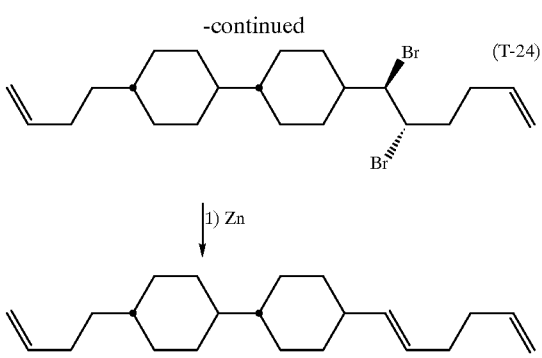

A mixture of 0.5 mol of a phosphonium salt (T-14), 0.52 mol of t-BuOK and 500 ml of THF was stirred at 0° C. or less for 2 hours to obtain a reddish yellow solution. While this solution was maintained at 0° C. or less, 300 ml of a THF solution containing 0.5 mol of a cyclohexanone derivative (T-13) was added dropwise, followed by stirring at room temperature for 1 hour. After the solvent was distilled off under reduced pressure, 1 l of heptane was added, and the precipitated crystals were removed by filtration. The solvent was removed from the resulting filtrate, and the residue was then purified by a column chromatography (toluene) to obtain 0.41 mol of a compound represented by (T-15).

A mixture of 0.4 mol of the compound (T-15) obtained by the above operation, 200 ml of ethanol, 500 ml of toluene and 5% of palladium carbon was stirred under a hydrogen atmosphere for 17 hours, and the catalyst was then removed by filtration. The resulting filtrate was concentrated to obtain a residue. This residue was recrystallized from hexane to obtain 0.21 mol of a compound represented by (T-16).

A mixture of 0.2 mol of the compound (T-16) obtained by the above operation, 20 ml of formic acid and 100 ml of toluene was refluxed for 1 hour, and then cooled to room temperature. After the reaction mixture was sufficiently washed with water, the organic layer was dried over anhydrous magnesium sulfate. Next, the solvent was removed under reduced pressure from the dried organic layer, and the resulting residue was then purified by a column chromatography (toluene) to obtain 0.17 mol of an aldehyde (T-17).

A mixture of 0.17 mol of a phosphonium salt (T-18), 0.18 mol of t-BuOK and 200 ml of THF was stirred for 1 hour, and 100 ml of a THF solution containing 0.15 mol of an aldehyde (T-17) was added dropwise at 10° C. or less, followed by stirring at room temperature for 2 hours. After the solvent was removed under reduced pressure from the resulting reaction mixture, 500 ml of heptane was added, and the precipitated crystals were then removed by filtration. Next, the solvent was removed from the filtrate, and the resulting residue was then purified by a column chromatography (toluene/heptane) to obtain 0.12 mol of an ester (T-19).

A mixture of 0.12 mol of the ester (T-19) and 200 ml of toluene was cooled to −60° C. or less, and after diisobutylaluminum hydride (toluene solution, corresponding to 0.13 mol) was added dropwise with stirring, 50 ml of methanol was added. Next, the solution was slowly returned to room temperature, and then poured into 200 ml of 3M hydrochloric acid. Insolubles in this solution were removed therefrom by filtration (using Celite), and the resulting organic layer was sufficiently washed with water, and then dried over anhydrous magnesium sulfate. The solvent in the dried organic layer was removed therefrom under reduced pressure, and the resulting residue was then purified by a

38 column chromatography (toluene) to obtain 0.10 mol of an aldehyde (T-20).

A mixture of 100 mmol of a phosphonium salt (T-21), 110 mmol of t-BuOK and 90 ml of THF was stirred for 1 hour, and 40 ml of a THF solution containing 100 mmol of an aldehyde (T-20) was then added dropwise at 0° C. or less, followed by stirring at room temperature for 2 hours. After the solvent was removed under reduced pressure, 300 ml of heptane was added, and the precipitated crystals were then removed by filtration. Next, the solvent was removed from the filtrate, and the resulting residue was then purified by a column chromatography (heptane) to obtain 96 mmol of a compound (T-22).

A mixture of 90 mmol of the compound (T-22) obtained by the above operation, 150 ml of methylene chloride, 0.6 mol of potassium carbonate and 99 mmol of metachloroperbenzoic acid was stirred at room temperature overnight. Afterward, 200 ml of water was added, followed by sufficient stirring. The separated organic layer was dried over anhydrous magnesium sulfate, and the solvent in the organic layer was removed therefrom to obtain 88 mmol of a crude compound (T-23).

A mixture of 88 mmol of the compound (T-23) obtained by the above operation, 180 ml of dibromotriphenylphospholane and 170 ml of toluene was stirred for 3 hours and then cooled to room temperature, and 300 ml of water was added thereto, followed by sufficient stirring. The separated organic layer was sufficiently washed with an aqueous saturated sodium hydrogencarbonate solution and water in turn, and then dried over anhydrous magnesium sulfate. Afterward, the solvent was removed under reduced pressure, and the resulting residue was purified by a column chromatography (toluene/hexane), and further recrystallized 4 times from a mixed solvent of benzene and ethanol to obtain 29 mmol of a dibromide (T-24).

A mixture of 25 mmol of the dibromide (T-24), 70 ml of acetic acid and 100 mmol of zinc was stirred at room temperature overnight, and 200 ml of water and 150 ml of heptane were added, followed by sufficient stirring. The separated organic layer was sufficiently washed with an aqueous saturated sodium hydrogencarbonate solution and water, and then dried over anhydrous magnesium sulfate. Afterward, the solvent was removed under reduced pressure, and the resulting residue was purified by a column chromatography (heptane), and further recrystallized from a mixed solvent of benzene and ethanol to obtain 16 mmol of the desired compound. A structure of the obtained compound was well supported by spectrum data.

EXAMPLE 2

A liquid crystal composition $B_1$ was prepared which was constituted of 24% by weight of 4-(4-propylcyclohexyl) benzonitrile, 36% by weight of 4-(4-pentylcyclohexyl) benzonitrile, 25% by weight of 4-(4-heptylcyclohexyl) benzonitrile, 15% by weight of 4'-(4-pentylcyclohexyl)-4-cyanobiphenyl.

A clearing point (an NI point), a dielectric anisotropy ($\Delta\epsilon$), an optical anisotropy ($\Delta n$) and a viscosity ($\eta$) of the composition $B_1$ were 71.7° C., 11.0, 0.137 and 27.3 mPa·s, respectively. In this connection, the viscosity ($\eta$) was measured at 20° C., and the optical anisotropy ($\Delta n$) and the dielectric anisotropy ($\Delta\epsilon$) were measured at 25° C.

85% by weight of $B_1$ was mixed with 15% by weight of 4'-(1,5-hexadienyl)-4-(3-butenyl)bicyclohexane [a compound having the general formula (1) in which $R_1$ is 1,5-hexadienyl, $R_2$ is 3-butenyl, p=q=0, ring $A_3$=ring $A_4$ is 1,4-cyclohexylene, and $Z_3$ is a single bond] prepared in Example 1 to obtain a liquid crystal composition $A_1$. A dielectric anisotropy ($\Delta\epsilon$), an optical anisotropy ($\Delta n$) and a viscosity ($\eta$) of the composition $A_1$ were 9.6, 0.124 and 19.2 mPa·s, respectively. In this connection, the viscosity ($\eta$) was measured at 20° C., and the optical anisotropy ($\Delta n$) and the dielectric anisotropy ($\Delta\epsilon$) were measured at 25° C.

EXAMPLE 3

Compounds shown in Tables 1 to 10 were prepared in accordance with the procedure of Example 1. With regard to a part of these prepared compounds, 15% by weight of each of the prepared compounds regarding the present invention was mixed with 85% by weight of the compound $B_1$ formed by the same procedure as in Example 2 to prepare a liquid crystal composition. In addition, a dielectric anisotropy ($\Delta\epsilon$), an optical anisotropy ($\Delta n$) and a viscosity ($\eta$) of each of the liquid crystal compositions are shown in tables. In this connection, the viscosity ($\eta$) was measured at 20° C., and the optical anisotropy ($\Delta n$) and the dielectric anisotropy ($\Delta\epsilon$) were measured at 25° C.

Of the compounds represented by the general formula (1), the compounds of p=q=0 are shown in Tables 1, 2 and 3.

TABLE 1

| $A_3$ | $Z_3$ | $A_4$ | $R_1$ | $R_2$ | |
|---|---|---|---|---|---|
| ⬡ | — | ⬡ | \_/⎯ | ⎯\\ | $\Delta\epsilon = 9.7, \Delta n = 0.131$ <br> $\eta = 10.4$ mPas |
| ⬡ | — | ⬡ | \_/⎯ | ⎯\_ | |
| ⬡ | — | ⬡ | \_/⎯ | ⎯\\/⎯F | |
| ⬡ | — | ⬡ | \_/⎯ | ⎯\\_// | |
| ⬡ | — | ⬡ | \_/⎯ | ⎯\\_/⎯ | |
| ⬡ | — | ⬡ | =\\_/⎯ | ⎯\\ | $\Delta\epsilon = 9.6, \Delta n = 0.129$ <br> $\eta = 19.0$ mPas |
| ⬡ | — | ⬡ | =\\_/⎯ | ⎯\\_// | |
| ⬡ | — | ⬡ | //\\_// | ⎯\\ | $\Delta\epsilon = 9.6, \Delta n = 0.127$ <br> $\eta = 19.0$ mPas <br> S25N60.0I |
| w⬡ | — | ⬡ | //\\_/⎯ | ⎯\\_// | $\Delta\epsilon = 9.5, \Delta n = 0.126$ <br> $\eta = 20.0$ mPas <br> C-38.6S73.7N83.6I |
| ⬡ | — | ⬡ | //\\_/⎯ | ⎯\\_/⎯F | $\Delta\epsilon = 10.2, \Delta n = 0.126$ <br> $\eta = 23.0$ mPas |

TABLE 1-continued
| $A_3$ | $Z_3$ | $A_4$ | $R_1$ | $R_2$ | |
|---|---|---|---|---|---|
|  | — |  |  |  | Δε = 9.6, Δn = 0.127<br>η = 19.3 mPas |
|  | — | 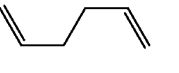 |  |  | |
|  | — | 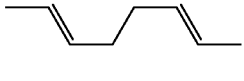 |  | —CH$_3$ | |
|  | — |  |  |  | |
|  | — |  |  |  | Δε = 9.6, Δn = 0.128<br>η = 19.2 mPas |
|  | — | 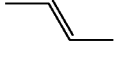 |  |  | |
|  | — | 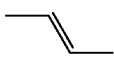 |  |  | |
| 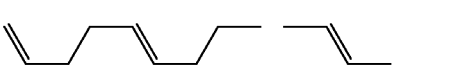 | — | 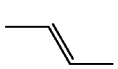 |  |  | |
TABLE 2
| $A_3$ | $Z_3$ | $A_4$ | $R_1$ | $R_2$ |
|---|---|---|---|---|
|  | — | 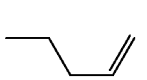 |  |  |
|  | — |  |  | 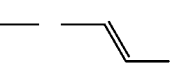 |
|  | — |  | 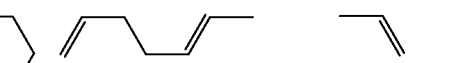 |  |

TABLE 2-continued
| $A_3$ | $Z_3$ | $A_4$ | $R_1$ | $R_2$ | |
|---|---|---|---|---|---|
|  | — |  |  |  | |
|  | — |  | 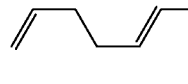 |  | |
|  | — | 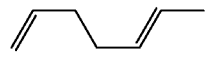 |  |  | |
|  | — |  |  | 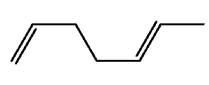 | |
|  | — |  | 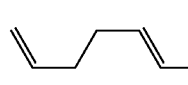 |  | |
|  | — | 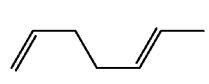 |  |  | |
| 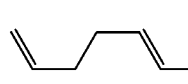 | — |  |  | 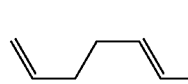 | |
|  | — |  | 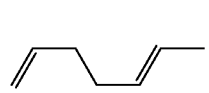 |  | |
|  | CH$_2$CH$_2$ | 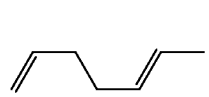 |  |  | |
| 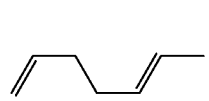 | CH$_2$CH$_2$ |  |  | 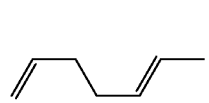 | |
|  | CH=CH |  | 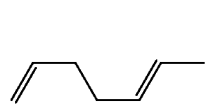 |  | Δε = 9.5, Δn = 0.126<br>η = 20.2 mPas<br>C42.5N65.2I |
|  | CH=CH |  |  |  | |
|  | CH=CH |  |  | F | |

TABLE 2-continued
| $A_3$ $Z_3$ | $A_4$ $R_1$ | $R_2$ |
|---|---|---|
|  CH=CH |  |  F |
TABLE 3
| $A_3$ $Z_3$ | $A_4$ $R_1$ | $R_2$ |
|---|---|---|
|  CH=CH |  |  |
| 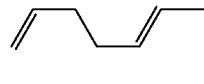 CH=CH |  |  |
|  CH=CH |  |  |
|  CH$_2$O | 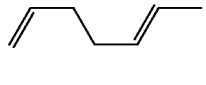 |  |
|  OCH$_2$ | 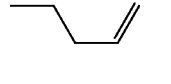 |  |
|  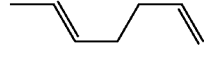 |  |  |
|   |  |  |
|  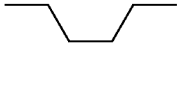 |  |  |
|  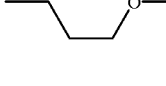 |  |  |

TABLE 3-continued
| A₃ / Z₃ | A₄ / R₁ | R₂ |
|---|---|---|
|  |   |  |
|  CH₃ |   |  |
|  CH₃ |   |  |
|  CF₂O |   |  |
|  OCF₂ |   |  |
|  CF=CF |   |  |
|  CF=CF |   |  |
|  CF=CF |   |  |
Of the compounds represented by the general formula (1), the compounds of p=0 and q=1 are shown in Tables 4, 5 and 6.
TABLE 4
| A₂ / Z₂ | A₃ / Z₃ | A₄ / R₁ | R₂ |
|---|---|---|---|
|  — |  — |   |  |
|  — |  — |   |  |

TABLE 4-continued
| $A_2$ | $Z_2$ | $A_3$ | $Z_3$ | $A_4$ | $R_1$ | $R_2$ | |
|---|---|---|---|---|---|---|---|
|  | — |  | — |  |  |  | |
|  | — | 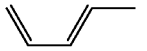 | — |  |  |  | Δ ε = 9.6<br>Δ n = 0.133 |
|  | — |  | — |  |  |  | |
|  | — | 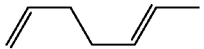 | — |  |  |  | |
|  | — |  | — |  |  |  | |
|  | — |  | — |  |  |  | |
|  | — | 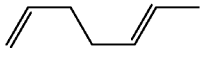 | — |  |  |  | |
|  | — |  | — |  |  |  | |
|  | — |  | — |  |  |  | |
|  | — |  | — |  |  |  | |
|  | — | 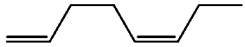 | — |  |  |  | |
|  | — |  | — |  |  |  | |

TABLE 4-continued
| A₂ | Z₂ | A₃ | Z₃ | A₄ | R₁ | R₂ |
|---|---|---|---|---|---|---|
|  | — |  | — |  |  |  |
|  | — | 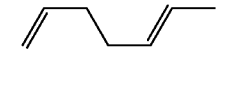 | — | 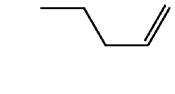 |  |  |
|  | — | 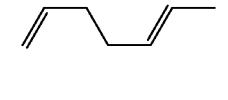 | — | 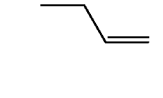 |  |  |
TABLE 5
| A₂ | Z₂ | A₃ | Z₃ | A₄ | R₁ | R₂ |
|---|---|---|---|---|---|---|
|  | — | 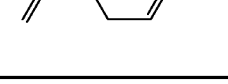 | — | 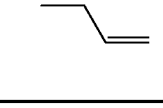 |  |  |
|  | — |  | — | 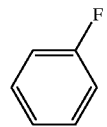 |  | 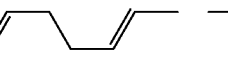 |
|  | CH=CH |  | — | 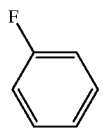 |  | 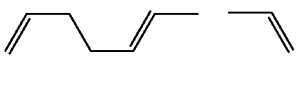 |
|  | — |  | CH=CH |  |  | 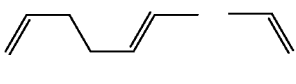 |
|  | CH=CH |  | CH=CH |  |  | 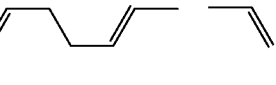 |
|  | CH=CH |  | CH=CH |  |  | 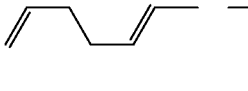 |
|  | CH₂CH₂ |  | CH=CH |  |  | 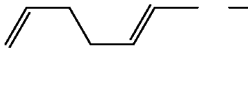 |

TABLE 5-continued
| A₂ | Z₂ | A₃ | Z₃ | A₄ | R₁ | R₂ |
|---|---|---|---|---|---|---|
|  |  |  | CH=CH |  |  |  |
|  | CH=CH |  | CH=CH |  |  |  |
|  |  |  | CH=CH |  |  |  |
|  | — |  | CH2CH2 |  |  |  |
|  | — |  | OCH2 |  |  |  |
|  | CH2CH2 |  | — |  |  |  |
|  | CH2CH2 |  | — |  |  |  |
|  | CH2CH2 |  | CF2O |  |  |  |
|  | CH2CH2 |  | CF=CF |  |  |  |
|  | CH=CH |  | — |  |  |  |
TABLE 6
| A₂ | Z₂ | A₃ | Z₃ | A₄ | R₁ | R₂ |
|---|---|---|---|---|---|---|
|  | CF=CF |  | CF=CF |  |  |  |

TABLE 6-continued
| A₂ / Z₂ | A₃ / Z₃ | A₄ | R₁ | R₂ |
|---|---|---|---|---|
|  CH=CH |  — |  |  |  |
|  CH=CH | 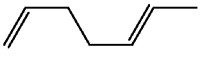 — | 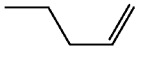 |  |  |
|  CH=CH | 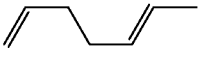 — | 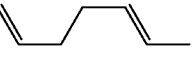 |  |  |
|  | 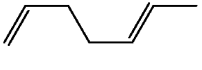 — |  |  | 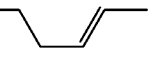 |
|  |  — | 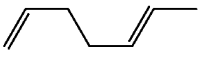 | 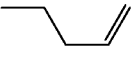 |  |
| 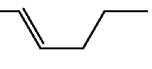 CH₂CH₂ |  — |  | 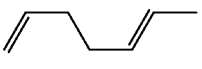 | 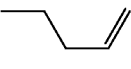 |
|  CH₂CH₂ |  — |  | 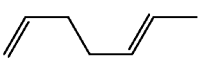 | 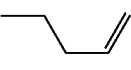 |
|  CH₂CH₂ |  — |  | 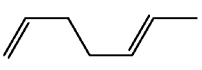 | 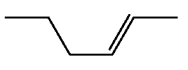 |
|  — |  CH2CH2 |  | 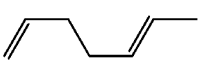 | 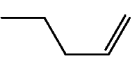 |
|  — |  CH2CH2 |  | 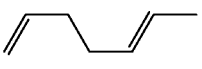 | 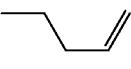 |
|  CH₂CH₂ |  — |  | 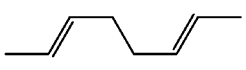 | 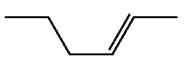 |
|  CH₂CH₂ |  — |  | 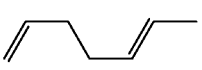 | 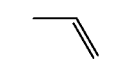 |

TABLE 6-continued

Of the compounds represented by the general formula (1), the compounds of p=1 and q=1 are shown in Tables 7, 8, 9 and 10.

TABLE 7

TABLE 7-continued

| A₁ | Z₁ | A₂ | Z₂ | A₃ | Z₃ | A₄ | R₁ | R₂ |
|---|---|---|---|---|---|---|---|---|

TABLE 8

| A₁ | Z₁ | A₂ | Z₂ | A₃ | Z₃ | A₄ | R₁ | R₂ |
|---|---|---|---|---|---|---|---|---|

TABLE 8-continued

| A₁ | Z₁ | A₂ | Z₂ | A₃ | Z₃ | A₄ | R₁ | R₂ |
|---|---|---|---|---|---|---|---|---|
| ⬡ | — | ⬡ | — | pyrimidine | — | ⬡ | ⌇⌇⌇ | ⌇⌇ |
| ⬡ | — | ⬡ | CH₂CH₂ | ⬡ | — | ⬡ | ⌇⌇⌇ | ⌇⌇ |
| ⬡ | — | ⬡ | (CH₂)₄ | ⬡ | — | ⬡ | ⌇⌇⌇ | ⌇⌇ |
| ⬡ | CH=CH | ⬡ | — | ⬡ | — | ⬡ | ⌇⌇⌇ | ⌇⌇ |

TABLE 9

| A₁ | Z₁ | A₂ | Z₂ | A₃ | Z₃ | A₄ | R₁ | R₂ |
|---|---|---|---|---|---|---|---|---|
| ⬡ | — | ⬡ | CH=CH | ⬡ | — | ⬡ | ⌇⌇⌇ | ⌇⌇ |
| ⬡ | CH=CH | ⬡ | CH=CH | ⬡ | — | ⬡ | ⌇⌇⌇ | ⌇⌇ |
| ⬡ | — | ⬡ | — | ⬡ | CF=CF | ⬡ | ⌇⌇⌇ | ⌇⌇ |
| ⬡ | — | ⬡ | — | ⬡ | CF₂O | ⬡ | ⌇⌇⌇ | ⌇⌇ |
| ⬡ | — | ⬡ | CH=CH | ⬡ | — | ⬡ | ⌇⌇⌇ | ⌇⌇ |
| ⬡ | — | ⬡ | CF2O | ⬡ | — | ⬡ | ⌇⌇⌇ | ⌇⌇ |
| ⬡ | — | ⬡ | OCF2 | ⬡ | — | ⬡ | ⌇⌇⌇ | ⌇⌇ |

TABLE 9-continued

| $A_1$ | $Z_1$ | $A_2$ | $Z_2$ | $A_3$ | $Z_3$ | $A_4$ | $R_1$ | $R_2$ |
|---|---|---|---|---|---|---|---|---|
| ⬡ | — | ⬡F | OCF2 | ⬡ | — | ⬡ | ⁄＼⁄ | ＼⁄ |
| ⬡ | — | ⬡F,F | OCF2 | ⬡ | — | ⬡ | ⁄＼⁄ | ＼⁄ |

TABLE 10

| $A_1$ | $Z_1$ | $A_2$ | $Z_2$ | $A_3$ | $Z_3$ | $A_4$ | $R_1$ | $R_2$ |
|---|---|---|---|---|---|---|---|---|
| ⬡ | CH₂CH₂ | ⬡ | CF2O | ⬡ | — | ⬡ | ⁄＼⁄ | ＼⁄ |
| ⬡ | CH₂CH₂ | ⬡ | — | ⬡ | — | pyrimidine | ⁄＼⁄ | ＼⁄ |
| ⬡ | CH₂CH₂ | ⬡ | — | ⬡ | — | pyridine | ⁄＼⁄ | ＼⁄ |
| ⬡ | CH=CH | ⬡ | — | ⬡ | — | pyrazine | ⁄＼⁄ | ＼⁄ |
| ⬡ | CH=CH | ⬡ | — | ⬡ | — | pyrimidine | ⁄＼⁄⁄ | ＼⁄＼⁄ |

Next, the liquid crystal compositions prepared by the use of the compounds represented by the general formula (1) of the present invention will be described in Examples 4 to 29. However, the compounds used in the following examples are represented by the use of symbols which are defined in Table 11. Furthermore, in the following partial structural formula

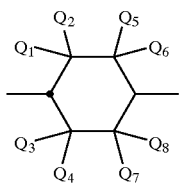

for example, in the case that the hydrogen atoms of trans-1,4-cyclohexylene are substituted by deuterium at positions $Q_1$, $Q_2$ and $Q_3$, it is represented by a symbol H[1D,2D,3D], or in the case that they are substituted by deuterium at positions $Q_5$, $Q_6$ and $Q_7$, it is represented by a symbol H[5D,6D,7D]. Thus, the substitution positions of deuterium are shown by the numbers in the brackets [ ].

Incidentally, a viscosity η was measured at 20° C., and a refractive index anisotropy value Δn, a dielectric anisotropy value Δε, a threshold voltage Vth and a twist pitch length P were measured at 25° C., respectively. In addition, % is based on weight.

TABLE 11

Representation of Compounds by Use of Symbols
R—(A₁)—Z₁— . . . —Zₙ—(Aₙ)—X

1) Left Terminal Group R—

| Group | Symbol |
|---|---|
| $C_nH_{2n+1}$— | n- |
| $C_nH_{2n+1}O$— | nO- |
| $C_nH_{2n+1}OC_mH_{2m}$— | nOm- |
| $CH_2=CH$— | V- |
| $CH_2=CHC_nH_{2n}$— | Vn- |
| $C_nH_{2n+1}CH=CHC_mH_{2m}$— | nVm- |
| $C_nH_{2n+1}CH=CHC_mH_{2m}CH=CHC_kH_{2k}$— | nVmVk- |

2) Ring Structure —(A₁)—, —(Aₙ)—

| Structure | Symbol |
|---|---|
| 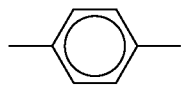 | B |
| 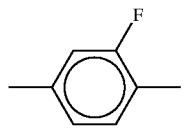 | B(F) |
| 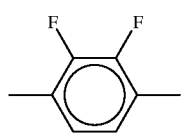 | B(2F, 3F) |
| 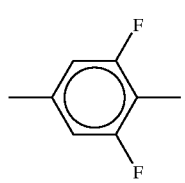 | B(F, F) |
| 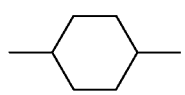 | H |
| 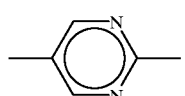 | Py |
| 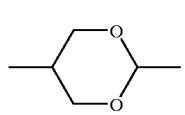 | D |

TABLE 11-continued

| Structure | Symbol |
|---|---|
| (cyclohexenylene) | Ch |

3) Bond Group —Z₁—, —Zₙ—

| Group | Symbol |
|---|---|
| —$C_2H_4$— | 2 |
| —$C_4H_8$— | 4 |
| —COO— | E |
| —C≡C— | T |
| —CH=CH— | V |
| —$CF_2O$— | CF2O |
| —$OCF_2$— | OCF2 |

4) Right Terminal Group —X

| Group | Symbol |
|---|---|
| —F | —F |
| —Cl | —CL |
| —CN | —C |
| —$CF_3$ | —CF3 |
| —$OCF_3$ | —OCF3 |
| —$OCF_2H$ | —OCF2H |
| —$C_nH_{2n+1}$ | -n |
| —$OC_nH_{2n+1}$ | -On |
| —$COOCH_3$ | -EMe |
| —$C_nH_{2n}CH=CH_2$ | -nV |
| —$C_mH_{2m}CH=CHC_nH_{2n+1}$ | -mVn |
| —$C_mH_{2m}CH=CHC_nH_{2n}F$ | -mVnF |
| —CH=$CF_2$ | -VFF |
| —$C_nH_{2n}CH=CF_2$ | -nVFF |
| —C≡C—CN | -TC |

5) Examples of Representation

Ex. 1    3-H2B(F, F)B(F)-F $C_3H_7$-[cyclohexyl]-$C_2H_4$-[phenyl(F,F)]-[phenyl(F,F)]-F Ex. 2    3-HB(F)TB-2

$C_3H_7$-[cyclohexyl]-[phenyl(F)]-C≡C-[phenyl]-$C_2H_5$

Ex. 3    1V2-BEB(F, F)-C $CH_3CH=CHCH_2CH_2$-[phenyl]-COO-[phenyl(F,F)]-CN

Example 4

| | |
|---|---|
| V2V-HH-2V | 8.0% |
| 1V2-BEB (F,F)-C | 5.0% |
| 3-HB-C | 25.0% |
| 1-BTB-3 | 5.0% |
| 2-BTB-1 | 10.0% |

TABLE 11-continued

| | |
|---|---|
| 3-HH-4 | 3.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |
| $T_{N1}$ = 91.9 (° C.) | |
| $\eta$ = 13.6 (mPa · s) | |
| $\Delta n$ = 0.165 | |
| $\Delta\epsilon$ = 7.1 | |
| Vth = 2.09 (V) | |
| Example 5 | |
| V2V-HH-2V | 10.0% |
| V2-HB-C | 12.0% |
| 1V2-HB-C | 12.0% |
| 3-HB-C | 15.0% |
| 3-H [1D, 2D, 3D] H-C | 9.0% |
| 3-HB (F)-C | 5.0% |
| 2-BTB-1 | 2.0% |
| 3-HH-4 | 2.0% |
| 3-HH-VFF | 2.0% |
| 2-H [1D, 2D, 3D] HB-C | 3.0% |
| 3-HHB-C | 6.0% |
| 3-HB (F) TB-2 | 8.0% |
| 3-H2BTB-2 | 5.0% |
| 3-H2BTB-3 | 5.0% |
| 3-H2BTB-4 | 4.0% |
| $T_{N1}$ = 90.4 (° C.) | |
| $\eta$ = 10.8 (mPa · s) | |
| $\Delta n$ = 0.157 | |
| $\Delta\epsilon$ = 8.8 | |
| Vth = 1.98 (V) | |
| Example 6 | |
| V2V-HHB-2V | 8.0% |
| 2O1-BEB (F)-C | 5.0% |
| 3O1-BEB (F)-C | 15.0% |
| 4O1-BEB (F)-C | 13.0% |
| 5O1-BEB (F)-C | 13.0% |
| 2-HHB (F)-C | 15.0% |
| 3-HHB (F)-C | 15.0% |
| 3-HB (F) TB-2 | 4.0% |
| 3-HB (F) TB-3 | 4.0% |
| 3-HB (F) TB-4 | 4.0% |
| 3-HHB-O1 | 4.0% |
| Example 7 | |
| V2V-HHB-2V | 8.0% |
| 5-PyB-F | 4.0% |
| 3-PyB (F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| Example 8 | |
| V2V-HH-V2F | 5.0% |
| V2V-HH-V2V | 5.0% |
| 3-DB-C | 10.0% |
| 4-DB-C | 10.0% |
| 2-BEB-C | 12.0% |
| 3-BEB-C | 4.0% |
| 3-PyB (F)-F | 6.0% |
| 4-HEB-O2 | 4.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |
| Example 9 | |
| V2V-HH-2V | 5.0% |
| 3-HB-C | 18.0% |
| 7-HB-C | 3.0% |
| 1O1-HB-C | 10.0% |
| 3-HB (F)-C | 10.0% |
| 2-PyB-2 | 2.0% |
| 3-PyB-2 | 2.0% |
| 4-PyB-2 | 2.0% |
| 1O1-HH-3 | 2.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| $T_{N1}$ = 81.3 (° C.) | |
| $\eta$ = 17.0 (mPa · s) | |
| $\Delta n$ = 0.142 | |
| $\Delta\epsilon$ = 8.1 | |
| Vth = 1.75 (V) | |
| Example 10 | |
| VV-HH-V | 7.0% |
| V2V-HHB-2V | 10.0% |
| 2O1-BEB (F)-C | 5.0% |
| 3O1-BEB (F)-C | 12.0% |
| 5O1-BEB (F)-C | 4.0% |
| 1V2-BEB (F, F)-C | 10.0% |
| 3-HH-EMe | 3.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB (F)-C | 2.0% |
| 3-HB (F) EB (F)-C | 2.0% |
| 3-HBEB (F, F)-C | 2.0% |
| 3-HHB-F | 4.0% |
| 3-HHB-O1 | 4.0% |
| 3-HHB-3 | 3.0% |
| 3-HEBEB-F | 2.0% |
| 3-HEBEB-1 | 2.0% |
| Example 11 | |
| V2V-HH-V | 8.0% |
| V2V-HH-2V | 8.0% |
| V2V-HHB-2V | 10.0% |
| 5-BEB (F)-C | 5.0% |
| V-HB-C | 11.0% |
| 5-PyB-C | 6.0% |
| 4-BB-3 | 11.0% |
| 5-HH-V | 5.0% |
| V-HHB-1 | 7.0% |
| V2-HHB-1 | 5.0% |
| 3-HHB-1 | 9.0% |
| 1V2-HBB-2 | 10.0% |
| 3-HHEBH-3 | 5.0% |

TABLE 11-continued

Example 12

| | |
|---|---|
| V2V-HHB-2V | 8.0% |
| 2O1-BEB (F)-C | 5.0% |
| 3O1-BEB (F)-C | 12.0% |
| 5O1-BEB (F)-C | 4.0% |
| 1V2-BEB (F, F)-C | 16.0% |
| 3-HB-O2 | 10.0% |
| 3-HH-4 | 3.0% |
| 3-HHB-F | 3.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB (F) TB-2 | 5.0% |

Example 13

| | |
|---|---|
| V2V-HH-V | 5.0% |
| V2V-HHB-2V | 5.0% |
| 2-BEB-C | 12.0% |
| 3-BEB-C | 4.0% |
| 4-BEB-C | 6.0% |
| 3-HB-C | 28.0% |
| 3-HEB-O4 | 7.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 2.0% |
| 3-HHB-O1 | 4.0% |

Example 14

| | |
|---|---|
| V2V-HH-V2F | 5.0% |
| V2V-HHB-2V | 13.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 10.0% |
| 1O-BEB-5 | 7.0% |
| 2-HHB-1 | 4.0% |
| 3-HHB-F | 4.0% |
| 3-HHB-1 | 7.0% |
| 3-HHB-O1 | 4.0% |

Example 15

| | |
|---|---|
| V2V-HH-2B | 15.0% |
| V2V-HHB-2V | 15.0% |
| 1V2-BEB (F, F)-C | 8.0% |
| 3-HB-C | 10.0% |
| V2V-HB-C | 14.0% |
| V2V-HH-3 | 4.0% |
| 3-HB-O2 | 4.0% |
| 3-HHB-1 | 10.0% |
| 3-HB (F) TB-2 | 4.0% |
| 3-HB (F) TB-3 | 4.0% |
| 3-H2BTB-2 | 4.0% |
| 3-H2BTB-3 | 4.0% |
| 3-H2BTB-4 | 4.0% |

Example 16

| | |
|---|---|
| V2V-HH-V | 3.0% |
| V2V-HHB-2V | 5.0% |
| V2V-HHB-1V | 6.0% |
| 5-BTB (F) TB-3 | 10.0% |
| V2-HB-TC | 10.0% |
| 3-HB-TC | 10.0% |
| 3-HB-C | 10.0% |
| 5-HB-C | 7.0% |
| 5-BB-C | 3.0% |
| 2-BTB-1 | 10.0% |
| 2-BTB-O1 | 5.0% |
| 3-HH-4 | 2.0% |
| 3-HHB-1 | 10.0% |
| 3-H2BTB-2 | 3.0% |
| 3-H2BTB-3 | 3.0% |
| 3-HB (F) TB-2 | 3.0% |

Example 17

| | |
|---|---|
| VV-HH-V | 7.0% |
| V1V-HH-V | 5.0% |
| V2V-HH-V | 10.0% |
| V2V-HH-V2F | 5.0% |
| V2V-HHB-2V | 13.0% |
| V2V-HHH-V | 4.0% |
| V2V-HBB-1V | 4.0% |
| 1V2-BEB (F, F)-C | 6.0% |
| 3-HB-C | 25.0% |
| 2-BTB-1 | 3.0% |
| 5-HH-VFF | 3.0% |
| 1-BHH-2VFF | 3.0% |
| 3-H2BTB-2 | 5.0% |
| 3-H2BTB-3 | 4.0% |
| 3-HHB-1 | 3.0% |

Example 18

| | |
|---|---|
| V2V-HHB-1V | 5.0% |
| V2V-HVHB-2V | 5.0% |
| V2V-HBB-1V | 5.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 4.0% |
| 3-HHEB-F | 4.0% |
| 5-HHEB-F | 4.0% |
| 2-HHB (F)-F | 7.0% |
| 3-HHB (F)-F | 7.0% |
| 5-HHB (F)-F | 7.0% |
| 3-HHB (F, F)-F | 5.0% |

Example 19

| | |
|---|---|
| V2V-HH-2V | 10.0% |
| 2-HHB (F)-F | 17.0% |
| 3-HHB (F)-F | 17.0% |
| 5-HHB (F)-F | 16.0% |
| 2-H2HB (F)-F | 10.0% |
| 3-H2HB (F)-F | 5.0% |
| 2-HBB (F)-F | 6.0% |
| 3-HBB (F)-F | 6.0% |
| 5-HBB (F)-F | 13.0% |

$T_{NI} = 98.0$ (° C.)
$\eta = 20.6$ (mPa · s)
$\Delta n = 0.094$
$\Delta \epsilon = 4.5$
$V_{th} = 2.41$ (V)

Example 20

| | |
|---|---|
| V2V-HHB-2V | 7.0% |
| 7-HB (F)-F | 5.0% |
| 5-H2B (F)-F | 5.0% |
| 3-HB-O2 | 10.0% |
| 3-HH-4 | 2.0% |
| 3-HH [5D, 6D, 7D]-4 | 3.0% |
| 2-HHB (F)-F | 10.0% |
| 3-HHB (F)-F | 10.0% |
| 5-HH [5D, 6D, 7D] B(F)-F | 10.0% |
| 3-H2HB (F)-F | 5.0% |
| 2-HBB (F)-F | 3.0% |
| 3-HBB (F)-F | 3.0% |
| 5-HBB (F)-F | 6.0% |
| 2-H2BB (F)-F | 5.0% |
| 3-H2BB (F)-F | 6.0% |
| 3-HHB-1 | 5.0% |
| 3-HHB-O1 | 5.0% |

Example 21

| | |
|---|---|
| V2V-HBB-1V | 7.0% |
| 7-HB (F, F)-F | 3.0% |
| 3-HB-O2 | 7.0% |
| 2-HHB (F)-F | 10.0% |
| 3-HHB (F)-F | 10.0% |

TABLE 11-continued

| | |
|---|---|
| 5-HHB (F)-F | 10.0% |
| 2-HBB (F)-F | 9.0% |
| 3-HBB (F)-F | 9.0% |
| 5-HBB (F)-F | 16.0% |
| 2-HBB-F | 4.0% |
| 3-HBB (F, F)-F | 5.0% |
| 5-HBB (F, F)-F | 10.0% |
| Example 22 | |
| | |
| V2V-HH-V | 5.0% |
| V2V-HH-2V | 5.0% |
| 7-HB (F, F)-F | 3.0% |
| 3-H2BH (F, F)-F | 12.0% |
| 4-H2HB (F, F)-F | 10.0% |
| 5-H2HB (F, F)-F | 10.0% |
| 3-HHB (F, F)-F | 5.0% |
| 4-HHB (F, F)-F | 5.0$ |
| 3-HH2B (F, F)-F | 15.0% |
| 3-HBB (F, F)-F | 12.0% |
| 5-HBB (F, F)-F | 12.0% |
| 3-HBCF2OB (F, F)-F | 6.0% |
| Example 23 | |
| | |
| V2V-HH-2V | 7.0% |
| V2V-HHB-1V | 3.0% |
| 7-HB (F, F)-F | 5.0% |
| 3-H2HB (F, F)-F | 12.0% |
| 3-HHB (F, F)-F | 10.0% |
| 4-HHB (F, F)-F | 5.0% |
| 3-HBB (F, F)-F | 10.0% |
| 3-HHEB (F, F)-F | 10.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 5.0% |
| 5-HBEB (F, F)-F | 3.0% |
| 3-HDB (F, F)-F | 15.0% |
| 3-HHBB (F, F)-F | 6.0% |
| Example 24 | |
| | |
| V2V-HH-V | 3.0% |
| V2V-HBB-1V | 4.0% |
| 3-HB-CL | 10.0% |
| 5-HB-CL | 4.0% |
| 7-HB-CL | 4.0% |
| 1O1-HH-5 | 2.0% |
| 2-HBB (F)-F | 8.0% |
| 3-HBB (F)-F | 8.0% |
| 5-HBB (F)-F | 14.0% |
| 4-HHB-CL | 8.0% |
| 5-HHB-CL | 8.0% |
| 3-H2HB (F)-CL | 4.0% |
| 3-HBB (F, F)-F | 10.0% |
| 5-H2BB (F, F)-F | 9.0% |
| 3-HB (F) VB-2 | 4.0% |
| Example 25 | |
| | |
| V2V-HH-V | 4.0% |
| V2V-HHB-2V | 4.0% |
| 3-HHB (F, F)-F | 9.0% |
| 3-H2HB (F, F)-F | 8.0% |
| 4-H2HB (F, F)-F | 8.0% |
| 5-H2HB (F, F)-F | 4.0% |
| 3-HBB (F, F)-F | 21.0% |
| 5-HBB (F, F)-F | 20.0% |
| 3-H2BB (F, F)-F | 10.0% |
| 5-HHBB (F, F)-F | 3.0% |
| 5-HHEBB-F | 2.0% |
| 3-HH2BB (F, F)-F | 3.0% |
| 1O1-HBBH-4 | 4.0% |
| Example 26 | |
| | |
| V2V-HH-V2F | 7.0% |
| V2V-HHB-2V | 5.0% |
| 5-HB-F | 12.0% |
| 6-HB-F | 2.0% |
| 7-HB-F | 7.0% |
| 2-HHB-OCF3 | 7.0% |
| 3-HHB-OCF3 | 7.0% |
| 4-HHB-OCF3 | 7.0% |
| 3-HH2B-OCF3 | 4.0% |
| 5-HH2B-OCF3 | 4.0% |
| 3-HHB (F, F)-OCF3 | 5.0% |
| 3-HBB (F)-F | 10.0% |
| 5-HBB (F)-F | 10.0% |
| 3-HH2B (F)-F | 3.0% |
| 3-HB (F) BH-3 | 3.0% |
| 5-HBBH-3 | 3.0% |
| 3-HHB (F, F)-OCF2H | 4.0% |
| Example 27 | |
| | |
| V2V-HH-2V | 5.0% |
| 5-H4HB (F, F)-F | 7.0% |
| 5-H4HB-OCF3 | 15.0% |
| 3-H4HB (F, F)-CF3 | 8.0% |
| 5-H4HB (F, F)-CF3 | 5.0% |
| 3-HB-CL | 6.0% |
| 5-HB-CL | 4.0% |
| 2-H2BB (F)-F | 5.0% |
| 3-H2BB (F)-F | 10.0% |
| 5-HVHB (F, F)-F | 5.0% |
| 3-HHB-OCF3 | 5.0% |
| 3-H2HB-OCF3 | 5.0% |
| V-HHB (F)-F | 5.0% |
| 3-HHB (F)-F | 5.0% |
| 5-HHEB-OCF3 | 2.0% |
| 3-HBEB (F, F)-F | 5.0% |
| 5-HH-V2F | 3.0% |
| $T_{NI} = 71.6$ (° C.) | |
| $\eta = 21.1$ (mPa · s) | |
| $\Delta n = 0.093$ | |
| $\Delta \epsilon = 7.7$ | |
| Vth = 1.81 (V) | |
| Example 28 | |
| | |
| V2V-HHB-2V | 3.0% |
| V2V-HBB-1V | 3.0% |
| 2-HHB (F)-F | 2.0% |
| 3-HHB (F)-F | 2.0% |
| 5-HHB (F)-F | 2.0% |
| 2-HBB (F)-F | 6.0% |
| 3-HBB (F)-F | 6.0% |
| 5-HBB (F)-F | 10.0% |
| 2-H2BB (F)-F | 9.0% |
| 3-H2BB (F)-F | 9.0% |
| 3-HBB (F, F)-F | 25.0% |
| 5-HBB (F, F)-F | 19.0% |
| 1O1-HBBH-5 | 4.0% |
| Example 29 | |
| | |
| V2V-HH-V | 4.0% |
| V2V-HHB-2V | 3.0% |
| 5-HB-CL | 12.0% |
| 3-HH-4 | 3.0% |
| 3-HB-O2 | 20.0% |
| 3-H2HB (F, F)-F | 8.0% |
| 3-HHB (F, F)-F | 8.0% |
| 3-HBB (F, F)-F | 6.0% |
| 2-HHB (F)-F | 5.0% |
| 3-HHB (F)-F | 5.0% |
| 5-HHB (F)-F | 5.0% |
| 2-H2HB (F)-F | 2.0% |
| 3-H2HB (F)-F | 1.0% |
| 5-H2HB (F)-F | 2.0% |
| 3-HHBB (F, F)-F | 4.0% |
| 3-HBCF2OB-OCF3 | 4.0% |
| 5-HBCF2OB (F, F)-CF3 | 4.0% |
| 3-HHB-1 | 2.0% |
| 3-HHB-O1 | 2.0% |
| Example 30 | |
| | |
| V2V-HH-V | 30.0% |
| V2V-HH-2V | 15.0% |
| V2VF-HVH-V | 5.0% |
| 1V2-BEB (F, F)-C | 5.0% |
| 3-HB-C | 25.0% |
| 3-HHB-1 | 6.0% |
| 3-H2BTB-2 | 4.0% |

TABLE 11-continued

| | |
|---|---:|
| 3-HHEB-F | 5.0% |
| 5-HHEB-F | 5.0% |
| $T_{N1}$ = 72.1 (° C.) | |
| $\Delta n$ = 0.096 | |
| $\Delta \epsilon$ = 5.5 | |
| Vth = 1.95 (V) | |
| Example 31 | |
| V2V-HH-V | 10.0% |
| V2V-HH-2V | 10.0% |
| 2O1-BEB (F)-C | 5.0% |
| 3O1-BEB (F)-C | 15.0% |
| 4O1-BEB (F)-C | 13.0% |
| 2-HHB (F)-C | 15.0% |
| 3-HHB (F)-C | 8.0% |
| 3-HB (F) TB-2 | 4.0% |
| 3-HB (F) TB-3 | 4.0% |
| 3-HB (F) TB-4 | 4.0% |
| 3-HHB-1 | 8.0% |
| 3-HHB-O1 | 4.0% |
| $T_{N1}$ = 96.0 (° C.) | |
| $\eta$ = 72.8 (mPa · s) | |
| $\Delta n$ = 0.138 | |
| $\Delta \epsilon$ = 26.4 | |
| Vth = 0.95 (V) | |
| Example 32 | |
| V2V-HVH-V | 8.0% |
| 5-PyB-F | 4.0% |
| 3-PyB (F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| $T_{N1}$ = 87.1 (° C.) | |
| $\eta$ = 32.3 (mPa · s) | |
| $\Delta n$ = 0.198 | |
| $\Delta \epsilon$ = 6.4 | |
| Vth = 2.18 (V) | |
| Example 33 | |
| V2V-HH-V | 6.0% |
| V2V-HVH-V | 6.0% |
| 2O1-BEB (F)-C | 5.0% |
| 3O1-BEB (F)-C | 12.0% |
| 5O1-BEB (F)-C | 4.0% |
| 1V2-BEB (F, F)-C | 10.0% |
| 3-HH-EMe | 10.0% |
| 3-HB-O2 | 6.0% |
| 7-HEB-F | 2.0% |
| 3-HHEB-F | 2.0% |
| 5-HHEB-F | 2.0% |
| 3-HBEB-F | 4.0% |
| 2O1-HBEB (F)-C | 2.0% |
| 3-HB (F) EB (F)-C | 2.0% |
| 3-HBEB (F, F)-C | 2.0% |
| 3-HHB-F | 4.0% |
| 3-HHB-O1 | 4.0% |
| 3-HHB-3 | 13.0% |
| 3-HEBEB-F | 2.0% |
| 3-HEBEB-1 | 2.0% |
| $T_{N1}$ = 81.1 (° C.) | |
| $\eta$ = 32.6 (mPa · s) | |
| $\Delta n$ = 0.114 | |
| $\Delta \epsilon$ = 23.5 | |
| Vth = 0.94 (V) | |
| Example 34 | |
| V2V-HH-V | 8.0% |
| 2O1-BEB (F)-C | 5.0% |
| 3O1-BEB (F)-C | 12.0% |
| 5O1-BEB (F)-C | 4.0% |
| 1V2-BEB (F, F)-C | 12.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-HB (F) TB-2 | 5.0% |
| $T_{N1}$ = 88.1 (° C.) | |
| $\eta$ = 37.8 (mPa · s) | |
| $\Delta n$ = 0.132 | |
| $\Delta \epsilon$ = 25.5 | |
| Vth = 1.06 (V) | |
| Example 35 | |
| V2V-HH-2V | 6.0% |
| V2V-HVH-V | 6.0% |
| 2-BEB-C | 12.0% |
| 3-BEB-C | 4.0% |
| 4-BEB-C | 6.0% |
| 3-HB-C | 16.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |
| $T_{N1}$ = 65.6 (° C.) | |
| $\eta$ = 20.9 (mPa · s) | |
| $\Delta n$ = 0.106 | |
| $\Delta \epsilon$ = 8.7 | |
| Vth = 2.09 (V) | |
| Example 36 | |
| V2V-HH-V | 4.0% |
| V2V-HH-2V | 4.0% |
| V2V-HVH-V | 4.0% |
| 2-BEB-C | 10.0% |
| 5-BB-C | 4.0% |
| 7-BB-C | 7.0% |
| 1-BTB-3 | 7.0% |
| 2-BTB-1 | 10.0% |
| 1O-BEB-2 | 10.0% |
| 1O-BEB-5 | 12.0% |
| 3-HHB-F | 4.0% |
| 3-HHB-1 | 7.0% |
| 3-HHB-O1 | 4.0% |
| 3-HHB-3 | 13.0% |
| $T_{N1}$ = 66.8 (° C.) | |
| $\eta$ = 15.3 (mPa · s) | |
| $\Delta n$ = 0.149 | |
| $\Delta \epsilon$ = 5.3 | |
| Vth = 2.11 (V) | |
| Example 37 | |
| V2V-HH-V | 12.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 9.0% |
| 3-HHEB-F | 4.0% |

TABLE 11-continued

| | |
|---|---|
| 5-HHEB-F | 4.0% |
| 2-HHB (F)-F | 7.0% |
| 3-HHB (F)-F | 7.0% |
| 3-HHB (F, F)-F | 5.0% |
| $T_{N1}$ = 94.8 (° C.) | |
| η = 13.4 (mPa · s) | |
| Δn = 0.097 | |
| Δε = 4.3 | |
| Vth = 2.63 (V) | |

Example 38

| | |
|---|---|
| V2V-HVH-V | 5.0% |
| 3-BEB (F)-C | 8.0% |
| 3-HB-C | 8.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |
| $T_{N1}$ = 94.1 (° C.) | |
| η = 14.1 (mPa · s) | |
| Δn = 0.124 | |
| Δε = 8.4 | |
| Vth = 2.13 (V) | |

Example 39

| | |
|---|---|
| V2V-HH-V | 6.0% |
| V2V-HH-2V | 6.0% |
| 7-HB (F, F)-F | 3.0% |
| 3-HB-O2 | 7.0% |
| 2-HHB (F)-F | 10.0% |
| 3-HHB (F)-F | 10.0% |
| 5-HHB (F)-F | 10.0% |
| 2-HBB (F)-F | 9.0% |
| 3-HBB (F)-F | 9.0% |
| 5-HBB (F)-F | 4.0% |
| 2-HBB-F | 4.0% |
| 3-HBB-F | 4.0% |
| 5-HBB-F | 3.0% |
| 3-HBB (F, F)-F | 5.0% |
| 5-HBB (F, F)-F | 10.0% |
| $T_{N1}$ = 82.3 (° C.) | |
| η = 19.3 (mPa · s) | |
| Δn = 0.107 | |
| Δε = 5.0 | |
| Vth = 2.22 (V) | |

Example 40

| | |
|---|---|
| V2V-HH-2V | 10.0% |
| V2V-HVH-V | 5.0% |
| 3-HHB (F, F)-F | 9.0% |
| 3-H2HB (F, F)-F | 8.0% |
| 4-H2HB (F, F)-F | 8.0% |
| 5-H2HB (F, F)-F | 8.0% |
| 3-HBB (F, F)-F | 21.0% |
| 5-HBB (F, F)-F | 5.0% |
| 3-H2BB (F, F)-F | 10.0% |
| 5-HHBB (F, F)-F | 3.0% |
| 5-HHEBB-F | 2.0% |
| 3-HH2BB (F, F)-F | 3.0% |
| 1O1-HBBH-4 | 4.0% |
| 1O1-HBBH-5 | 4.0% |
| $T_{N1}$ = 100.1 (° C.) | |
| η = 26.1 (mPa · s) | |
| Δn = 0.108 | |
| Δε = 7.4 | |
| Vth = 1.88 (V) | |

Example 41

| | |
|---|---|
| V2V-HH-2V | 5.0% |
| V2V-HVH-V | 5.0% |
| 5-HB-F | 12.0% |
| 6-HB-F | 9.0% |
| 7-HB-F | 7.0% |

TABLE 11-continued

| | |
|---|---|
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB (F, F)-OCF3 | 5.0% |
| 3-HBB (F)-F | 5.0% |
| 5-HBB (F)-F | 5.0% |
| 3-HH2B (F)-F | 3.0% |
| 3-HB (F) BH-3 | 3.0% |
| 5-HBBH-3 | 3.0% |
| 3-HHB (F, F)-OCF2H | 4.0% |
| $T_{N1}$ = 82.7 (° C.) | |
| η = 11.8 (mPa · s) | |
| Δn = 0.086 | |
| Δε = 4.0 | |
| Vth = 2.62 (V) | |

Example 42

| | |
|---|---|
| V2V-HH-V | 6.0% |
| 3-H2HB (F, F)-F | 7.0% |
| 5-H2HB (F, F)-F | 8.0% |
| 3-HHB (F, F)-F | 10.0% |
| 4-HHB (F, F)-F | 5.0% |
| 3-HH2B (F, F)-F | 9.0% |
| 5-HH2B (F, F)-F | 3.0% |
| 3-HBB (F, F)-F | 15.0% |
| 5-HBB (F, F)-F | 15.0% |
| 3-HBEB (F, F)-F | 2.0% |
| 4-HBEB (F, F)-F | 2.0% |
| 5-HBEB (F, F)-F | 2.0% |
| 3-HHEB (F, F)-F | 10.0% |
| 4-HHEB (F, F)-F | 3.0% |
| 5-HHEB (F, F)-F | 3.0% |
| $T_{N1}$ = 80.7 (° C.) | |
| η = 28.6 (mPa · s) | |
| Δn = 0.091 | |
| Δε = 10.8 | |
| Vth = 1.88 (V) | |

What is claimed is:

1. A compound represented by the general formula (1)

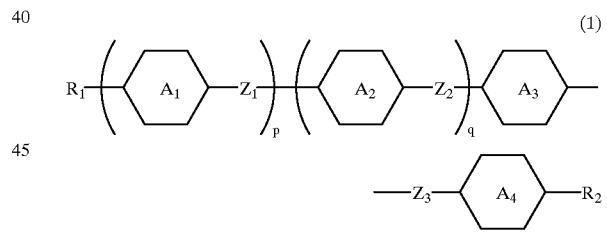

wherein $R_1$ is an alkadienyl group having 4 to 10 carbon atoms in which at least one hydrogen atom may be substituted by a fluorine atom, a chlorine atom or a cyano group; $R_2$ is an alkenyl group having 2 to 10 carbon atoms in which at least one hydrogen atom may be substituted by a fluorine atom, a chlorine atom or a cyano group; one or more non-adjacent methylene groups (—CH$_2$—) in the alkadienyl group or the alkenyl group may be replaced by —O—, —CH=CH— or —C≡C—; rings $A_1$, $A_2$, $A_3$ and $A_4$ are each independently 1,4-cyclohexylene, 1,4-cyclohexenylene, 1,4-phenylene, 1,3-dioxane-2,5-diyl, pyridine-2,5-diyl or pyrimidine-2,5-diyl in which at least one hydrogen atom may be substituted by a halogen atom; $Z_1$, $Z_2$ and $Z_3$ are each independently a single bond, —CH$_2$CH$_2$—, —CH=CH—, —C≡C—, —CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR=CH—, —CH=CR— or —CF=CF—, and R is an alkyl group having 1 to 5 carbon atoms; p and q are each independently 0 or 1.

2. The compound according to claim 1 wherein $R_1$ is a 1,3-alkadienyl group; and $R_2$ is an alkenyl group.

3. The compound according to claim 1 wherein $R_1$ is a 1,4-alkadienyl group; and $R_2$ is an alkenyl group.

4. The compound according to claim 1 wherein $R_1$ is a 1,5-alkadienyl group; and $R_2$ is an alkenyl group.

5. The compound according to claim 1 wherein $R_1$ is a 1,6-alkadienyl group; and $R_2$ is an alkenyl group.

6. The compound according to claim 1 wherein $R_1$ is a 3,7-alkadienyl group; and $R_2$ is an alkenyl group.

7. The compound according to claim 1 wherein $R_1$ and $R_2$ are each an alkadienyl group.

8. A liquid crystal composition comprising two or more components which contains at least one of the compounds described in any one of claims 1 to 7.

9. A liquid crystal composition which comprises, as a first component, at least one of the compounds described in any one of claims 1 to 7, and as a second component, at least one compound selected from the group consisting of compounds represented by the general formulae (2), (3) and (4)

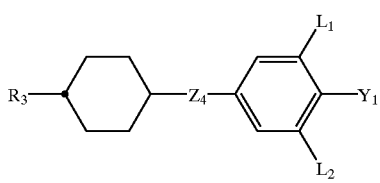

(2)

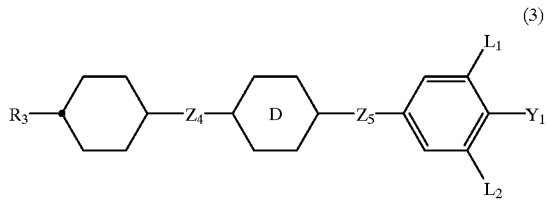

(3)

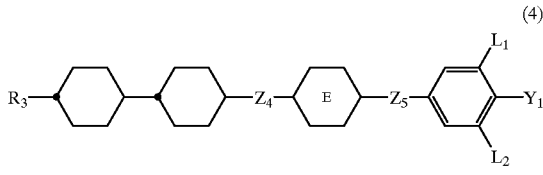

(4)

wherein $R_3$ is an alkyl group having 1 to 10 carbon atoms in which at least one hydrogen atom may be substituted by a fluorine atom, and one or more non-adjacent methylene groups (—CH$_2$—) in the alkyl group may be replaced by —O— or —CH=CH—; $Y_1$ is a fluorine atom, a chlorine atom, OCF$_3$, OCF$_2$H, CF$_3$, CF$_2$H, CFH$_2$, OCF$_2$CF$_2$H or OCF$_2$CFHCF$_3$; $L_1$ and $L_2$ are each independently a hydrogen atom or a fluorine atom; $Z_4$ and $Z_5$ are each independently a 1,2-ethylene group, a 1,4-butylene group, —COO—, —CF$_2$O—, —OCF$_2$—, —CH=—CH— or a single bond; a ring D is trans-1,4 -cyclohexylene, 1,3-dioxane-2,5-diyl or 1,4-phenylene in which at least one hydrogen atom may be substituted by a fluorine atom; a ring E is trans-1,4-cyclohexylene or 1,4-phenylene in which at least one hydrogen atom may be substituted by a fluorine atom.

10. A liquid crystal composition which comprises, as a first component, at least one of the compounds described in any one of claims 1 to 7, and as a second component, at least one compound selected from the group consisting of compounds represented by the general formulae (5) and (6)

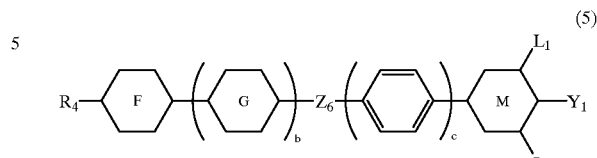

(5)

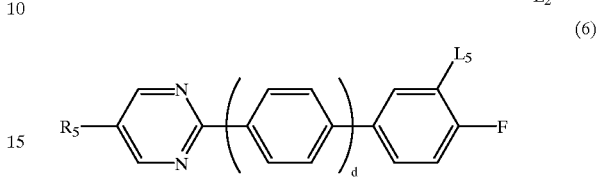

(6)

wherein $R_4$ and $R_5$ are each independently an alkyl group having 1 to 10 carbon atoms in which at least one hydrogen atom may be substituted by a fluorine atom, and one or more non-adjacent methylene groups (—CH$_2$—) in the alkyl group may be replaced by —O— or —CH=CH—; $Y_2$ is a —CN group or —C≡C—CN; a ring F is trans-1,4-cyclohexylene, 1,4 -phenylene, 1,3-dioxane-2,5-diyl or pyrimidine-2,5-diyl; a ring G is trans-1,4-cyclohexylene, 1,4-phenylene in which at least one hydrogen atom may be substituted by a fluorine atom, or pyrimidine-2,5-diyl; a ring M is trans-1,4-cyclohexylene or 1,4-phenylene; $Z_6$ is a 1,2-ethylene group, —COO— or a single bond; $L_3$, $L_4$ and $L_5$ are each independently a hydrogen atom or a fluorine atom; b, c and d are each independently 0 or 1.

11. A liquid crystal composition which comprises, as a first component, at least one of the compounds described in any one of claims 1 to 7; as a second component, at least one compound selected from the group consisting of the compounds represented by the general formulae (2), (3) and (4) described in claim 9; and as a third component, at least one compound selected from the group consisting of compounds represented by the general formulae (7), (8) and (9)

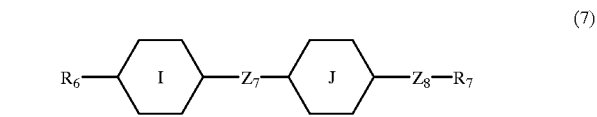

(7)

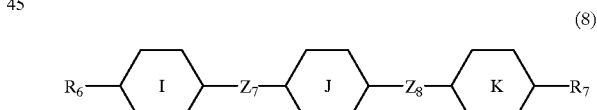

(8)

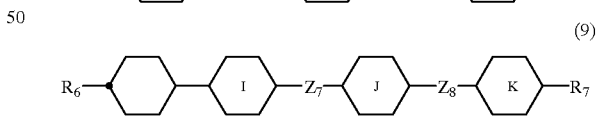

(9)

wherein $R_6$ and $R_7$ are each independently an alkyl group having 1 to 10 carbon atoms in which at least one hydrogen atom may be substituted by a fluorine atom, and one or more non-adjacent methylene groups (—CH$_2$—) in the alkyl group may be replaced by —O— or —CH=CH—; I, J and K are each independently trans-1,4-cyclohexylene, pyrimidine-2,5-diyl or 1,4-phenylene in which at least one hydrogen atom may be substituted by a fluorine atom; $Z_7$ and $Z_8$ are each independently —C≡C—, —COO—, —CH$_2$CH$_2$—, —CH=CH— or a single bond.

12. A liquid crystal composition which comprises, as a first component, at least one of the compounds described in any one of claims 1 to 7; as a second component, at least one compound selected from the group consisting of the compounds represented by the general formulae (5) and (6) described in claim 10; and as a third component, at least one compound selected from the group consisting of the compounds represented by the general formulae (7), (8) and (9) described in claim 11.

13. A liquid crystal composition which comprises, as a first component, at least one of the compounds described in any one of claims 1 to 7; as a second component, at least one compound selected from the group consisting of the compounds represented by the general formulae (2), (3) and (4) described in claim 9; as a third component, at least one compound selected from the group consisting of the compounds represented by the general formulae (5) and (6) described in claim 10; and as a fourth component, at least one compound selected from the group consisting of the compounds represented by the general formulae (7), (8) and (9) described in claim 11.

14. A liquid crystal composition comprising two or more components which contains at least one of the compounds described in any one of claims 1 to 7 and optionally comprising at least one optically active compound.

15. A liquid crystal composition which comprises, as a first component, at least one of the compounds described in any one of claims 1 to 7, and as a second component, at least one compound selected from the group consisting of compounds represented by the general formulae (2), (3) and (4)

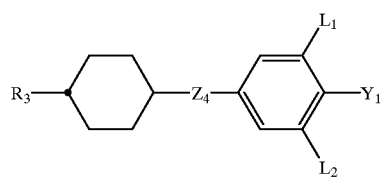

(2)

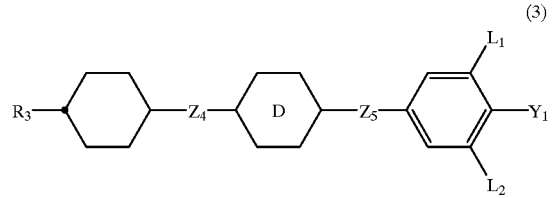

(3)

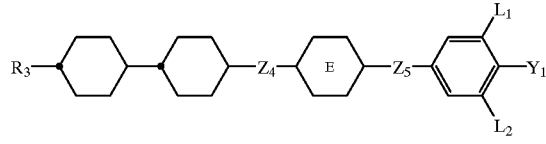

(4)

wherein $R_3$ is an alkyl group having 1 to 10 carbon atoms in which at least one hydrogen atom may be substituted by a fluorine atom, and one or more non-adjacent methylene groups (—$CH_2$—) in the alkyl group may be replaced by —O— or —CH=CH—; $Y_1$ is a fluorine atom, a chlorine atom, $OCF_3$, $OCF_2H$, $CF_3$, $CF_2H$, $CFH_2$, $OCF_2CF_2H$ or $OCF_2CFHCF_3$; $L_1$ and $L_2$ are each independently a hydrogen atom or a fluorine atom; $Z_4$ and $Z_5$ are each independently a 1,2-ethylene group, a 1,4-butylene group, —COO—, —$CF_2O$—, —$OCF_2$—, —CH=CH— or a single bond; a ring D is trans-1,4-cyclohexylene, 1,3-dioxane-2,5-diyl or 1,4-phenylene in which at least one hydrogen atom may be substituted by a fluorine atom; a ring E is trans-1,4-cyclohexylene or 1,4-phenylene in which at least one hydrogen atom may be substituted by a fluorine atom; and optionally further comprising at least one optically active compound as a third component.

16. A liquid crystal composition which comprises, as a first component, at least one of the compounds described in any one of claims 1 to 7, and as a second component, at least one compound selected from the group consisting of compounds represented by the general formulae (5) and (6)

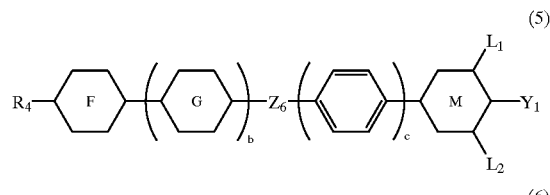

(5)

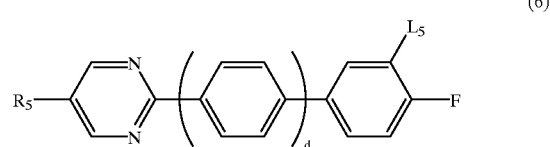

(6)

wherein $R_4$ and $R_5$ are each independently an alkyl group having 1 to 10 carbon atoms in which at least one hydrogen atom may be substituted by a fluorine atom, and one or more non-adjacent methylene groups (—$CH_2$—) in the alkyl group may be replaced by —O— or —CH=CH—; $Y_2$ is a —CN group or —C≡C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene in which at least one hydrogen atom may be substituted by a fluorine atom, or pyrimidine-2,5-diyl; a ring M is trans-1,4-cyclohexylene or 1,4-phenylene; $Z_6$ is a 1,2-ethylene group, —COO— or a single bond; $L_3$, $L_4$ and $L_5$ are each independently a hydrogen atom or a fluorine atom; b, c and d are each independently 0 or 1; and optionally further comprising at least one optically active compound as a third component.

17. A liquid crystal composition which comprises, as a first component, at least one of the compounds described in any one of claims 1 to 7; as a second component, at least one compound selected from the group consisting of the compounds represented by the general formulae (2), (3) and (4) described in claim 9; and as a third component, at least one compound selected from the group consisting of compounds represented by the general formulae (7), (8) and (9)

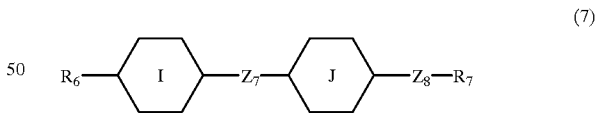

(7)

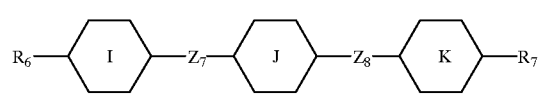

(8)

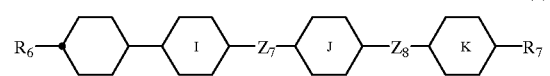

(9)

wherein $R_6$ and $R_7$ are each independently an alkyl group having 1 to 10 carbon atoms in which at least one hydrogen atom may be substituted by a fluorine atom, and one or more non-adjacent methylene groups (—$CH_2$—) in the alkyl group may be replaced by —O— or —CH=CH—; I, J and K are each independently trans-1,4-cyclohexylene, pyrimidine-2,5-diyl or 1,4-phenylene in which at least one hydrogen atom may be substituted by a fluorine atom; $Z_7$ and $Z_8$ are each independently —C≡C—, —COO—, —CH$_2$CH$_2$—, —CH=CH— or a single bond; and optionally further comprising at least one optically active compound as a fourth component.

18. A liquid crystal composition which comprises, as a first component, at least one of the compounds described in any one of claims 1 to 7; as a second component, at least one compound selected from the group consisting of the compounds represented by the general formulae (5) and (6) described in claim 10; and as a third component, at least one compound selected from the group consisting of the compounds represented by the general formulae (7), (8) and (9) described in claim 11, and optionally further comprising at least one optically active compound as a fourth component.

19. A liquid crystal composition which comprises, as a first component, at least one of the compounds described in any one of claims 1 to 7; as a second component, at least one compound selected from the group consisting of the compounds represented by the general formulae (2), (3) and (4) described in claim 9; as a third component, at least one compound selected from the group consisting of the compounds represented by the general formulae (5) and (6) described in claim 10; and as a fourth component, at least one compound selected from the group consisting of the compounds represented by the general formulae (7), (8) and (9) described in claim 11; and optionally further comprising at least one optically active compound as a fifth component.

20. A liquid crystal display device comprising the liquid crystal composition defined in claim 14.

* * * * *

UNITED STATES PATENT AND TRADEMARK OFFICE
CERTIFICATE OF CORRECTION

PATENT NO.    : 6,174,457 B1
DATED         : January 16, 2001
INVENTOR(S)   : Takashi Kato et al.

It is certified that error appears in the above-identified patent and that said Letters Patent is hereby corrected as shown below:

Column 1,
Line 28, correct "(s-i)" to -- (s-1) --.

Column 4,
Line 29, correct "–C ≡ –C–" to -- –C ≡ C– --.

Column 5,
Line 63, correct "–C ≡ –C–CN" to -- –C ≡ C–CN --.

Column 7,
Line 51, correct "$K_{33}/K11$" to -- $K_{33}/K_{11}$ --.

Column 36,
Delete "(T-12)" attached to the second formula.

Column 40,
Table 1, correct "$\eta$=10.4mPas" to -- $\eta$ = 19.4mPas --.

Column 60,
Table 8, correct the first $R_2$ " 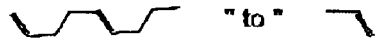 " to "  ".

Correct the 6th $R_2$ "  " to "  ".

Column 61,
Table 8-continued, correct the first A3 "  " to "  "

Table 9, correct 5th $z_2$ "CH=CH" to -- CF=CF --.

Column 69,
The first compound in Example 15, correct "V2V–HH–2B" to -- V2V–HH–2V --.

Column 72,
The third compound in Example 30, correct "V2VF–HVH–V" to -- V2V–HVH–V --.

UNITED STATES PATENT AND TRADEMARK OFFICE
CERTIFICATE OF CORRECTION

PATENT NO.      : 6,174,457 B1
DATED           : January 16, 2001
INVENTOR(S)     : Takashi Kato et al.

It is certified that error appears in the above-identified patent and that said Letters Patent is hereby corrected as shown below:

Column 77,
Line 58, correct "–CH=-CH–" to -- –CH=CH– --.

Columns 78 and 80,
Formula (5), correct "$L_1$" to -- $L_3$ --.
             correct "$L_2$" to -- $L_4$ --.
             correct "$Y_1$" to -- $Y_2$ --.
Formula (9), delete "$Z_8$".

Column 78,
Line 64, correct "$–C \equiv –C$" to -- $–C \equiv C–$ --.

Signed and Sealed this

Fifth Day of August, 2003

JAMES E. ROGAN
*Director of the United States Patent and Trademark Office*